(12) United States Patent
Maehara et al.

(10) Patent No.: US 9,000,202 B2
(45) Date of Patent: Apr. 7, 2015

(54) METHOD FOR PRODUCING INORGANIC OXIDE PARTICLES

(75) Inventors: Takayuki Maehara, Shunan (JP); Tadaharu Komatsubara, Shunan (JP); Yuya Yamano, Shunan (JP); Kenichi Ishizu, Shunan (JP); Makoto Sato, Shunan (JP); Hiroaki Taira, Shunan (JP); Hiroshi Kato, Shunan (JP)

(73) Assignee: Tokuyama Corporation, Shunan-Shi (JP)

( * ) Notice: Subject to any disclaimer, the term of this patent is extended or adjusted under 35 U.S.C. 154(b) by 300 days.

(21) Appl. No.: 13/579,798

(22) PCT Filed: Feb. 18, 2011

(86) PCT No.: PCT/JP2011/054216
§ 371 (c)(1),
(2), (4) Date: Aug. 17, 2012

(87) PCT Pub. No.: WO2011/102548
PCT Pub. Date: Aug. 25, 2011

(65) Prior Publication Data
US 2012/0323030 A1    Dec. 20, 2012

(30) Foreign Application Priority Data

Feb. 19, 2010 (JP) .................................. 2010-035111
May 28, 2010 (JP) .................................. 2010-122277
Jun. 30, 2010 (JP) .................................. 2010-149306

(51) Int. Cl.
*C07F 7/02* (2006.01)
*C01B 33/146* (2006.01)
*C01B 13/36* (2006.01)
*C01B 33/18* (2006.01)

(52) U.S. Cl.
CPC .............. *C01B 33/146* (2013.01); *C01B 13/36* (2013.01); *C01B 13/363* (2013.01); *C01B 33/18* (2013.01); *C01P 2004/52* (2013.01)

(58) Field of Classification Search
CPC ............................... C07F 7/10; C04B 35/589
USPC ........................................................ 546/412
See application file for complete search history.

(56) References Cited

U.S. PATENT DOCUMENTS

| | | | |
|---|---|---|---|
| 6,300,468 B1 * | 10/2001 | Bretz et al. .................... | 528/497 |
| 6,521,290 B1 | 2/2003 | Kudo et al. | |
| 6,555,282 B2 | 4/2003 | Okuno et al. | |
| 6,855,759 B2 | 2/2005 | Kudo et al. | |
| 2002/0061457 A1 * | 5/2002 | Okuno et al. .............. | 430/108.6 |

FOREIGN PATENT DOCUMENTS

| | | |
|---|---|---|
| CN | 1524787 A | 9/2004 |
| CN | 1757598 A | 4/2006 |
| EP | 959102 A2 * | 11/1999 |
| JP | 60-90811 A | 5/1985 |
| JP | 6-115925 A | 4/1994 |
| JP | 2000-44226 A | 2/2000 |
| JP | 2002-108001 A | 4/2002 |
| JP | 2003-277025 A | 10/2003 |
| JP | 2006-151764 A | 6/2006 |

OTHER PUBLICATIONS

International Search Report, issued in PCT/JP2011/054216, dated, May 17, 2011.
Forms PCT/IB/338, PCT/IB/373, and PCT/ISA/237 for International Application No. PCT/JP2011/054216 mailed Sep. 27, 2012.

* cited by examiner

*Primary Examiner* — Porfirio Nazario Gonzalez
*Assistant Examiner* — Kofi Adzamli
(74) *Attorney, Agent, or Firm* — Birch, Stewart, Kolasch & Birch, LLP

(57) ABSTRACT

The present invention relates to a method for producing inorganic oxide particles, comprising at least the following steps of:
coagulating a dispersion obtained by carrying out the hydrolysis reaction and the polycodensation reaction of a metal alkoxide in the presence of a basic catalyst;
filtering the dispersion to obtain particles; and
drying the particles, wherein
the step of coagulating the dispersion is carried out by adding a coagulant comprising at least one compound selected from the group consisting of carbon dioxide, ammonium carbonate, ammonium hydrogen carbonate and ammonium carbamate to the dispersion.

The inorganic oxide particles obtained by the method of the present invention have high purity and are excellent in flowability.

4 Claims, No Drawings

METHOD FOR PRODUCING INORGANIC OXIDE PARTICLES

TECHNICAL FIELD

The present invention relates to a method for producing inorganic oxide particles. More specifically, it relates to a method for producing inorganic oxide particles, which makes extremely easy the filtration and collection of inorganic oxide particles obtained by the hydrolysis and polycondensation reaction (so-called "sol-gel method") of a metal alkoxide in the presence of a basic catalyst.

BACKGROUND ART

The sol-gel method is known as one of the methods for producing inorganic oxide particles such as silica, titania, zirconia or alumina particles. This production method is to obtain inorganic oxide particles by the hydrolysis reaction and polycondensation reaction of a metal alkoxide such as tetraethoxysilane in an organic solvent containing water in the presence of an acidic catalyst or a basic catalyst. The sol-gel method is characterized in that fine inorganic oxide particles which are spherical and relatively uniform in particle size are obtained.

In a dispersion of inorganic oxide particles obtained by the reaction of the sol-gel method, the inorganic oxide particles are highly dispersed as fine primary particles. Therefore, it is extremely difficult to collect a cake (a concentrate of a dispersion containing inorganic oxide particles in high concentration) of inorganic oxide particles from this dispersion by filtration.

Then, to collect the cake from the above dispersion of inorganic oxide particles, for example, a method in which a dispersion medium is removed by heating and/or depressurizing the dispersion or a method in which the dispersion is centrifuged to spin down the inorganic oxide particles and then decantation is carried out is employed. The inorganic oxide particles can be obtained by drying the cake obtained by the above method to remove the dispersion medium remaining in the cake.

However, in the case of the above cake collection step, a firmly agglomerated product of the inorganic oxide particles contained in the cake is formed, and further a firm agglomerate of the inorganic oxide particles is formed by the subsequent drying step. Therefore, even when the inorganic oxide particles obtained by the above method are disintegrated, fine inorganic oxide particles which are uniform in particle size are not obtained. When the inorganic oxide particles are re-dispersed into a dispersion medium such as a resin or a solvent, the above agglomerate is not easily disintegrated by the shear of a disperser and not uniformly dispersed in a dispersion medium. Especially in the case of fine inorganic oxide particles having a primary particle diameter of 1 μm or less produced by the reaction of the sol-gel method, the cohesion force of the particles is very strong and an extremely firm agglomerate is apt to be formed.

To solve the above problem, various proposals have been made up till now.

For example, JP-A 6-115925 proposes a method in which inorganic oxide particles obtained by drying a dispersion of inorganic oxide particles are disintegrated by a jet mill. According to this method, it is possible to obtain inorganic oxide particles which are uniform in particle size to some extent but the number of firm agglomerates formed at the time of drying cannot be reduced. Therefore, it cannot be said that this is not the technology for basically solving the above problem.

JP-A 2003-277025 discloses a method for preventing agglomeration by adding ethylene glycol to a dispersion of inorganic oxide particles while a dispersion medium is removed from the dispersion so as to solve problems such as the agglomeration and sintering of a metal oxide without disintegration. According to this method, the formation of an agglomerate which is hardly disintegrated is suppressed but ethylene glycol may remain in the inorganic oxide particles unless the drying and calcination conditions are controlled precisely. Therefore, it is difficult to adopt this method according to the application purpose of the inorganic oxide particles.

Printing is becoming faster and picture quality is becoming higher in electrophotographic technologies for copiers and printers. Since the number of times of toner transfer increases in the copiers and printers, an additive for enhancing the transfer efficiency of a toner is becoming necessary. It is reported that sol-gel silica (surface treated inorganic oxide particles) which has a narrow particle size distribution and a hydrophobilized surface is effective as the above additive (JP-A 2002-108001).

To produce the sol-gel silica having a hydrophobized surface, there is proposed a method for obtaining hydrophobized silica by adding a silazane compound to silica sol to react it with the silica sol (JP-A 2006-151764). The collection of a cake of silica after hydrophobization in this method is carried out by distilling off a solvent from a dispersion containing surface treated silica. Although this collection method can be easily employed when silica is taken out from a flask in a laboratory scale, when this method is applied to an actual large-scale production plant, it is difficult to scrape out a cake of the hydrophobic sol-gel silica from a reaction oven, which is not practical. Although it is conceivable that a filtration method is employed to collect silica after hydrophobization, when the filtration method is employed to collect fine particles having a particle diameter of 1 μm or less such as the particles produced by the sol-gel method, the particles pass through a filter paper or a filter cloth. When the solvent is removed from the particles after filtration to dry the particles up, the hydrophobic sol-gel silica firmly agglomerate, whereby it may be difficult to re-disperse it.

DISCLOSURE OF THE INVENTION

The present invention was made in view of the above situation. That is, it is an object of the present invention to provide a method for easily producing inorganic oxide particles synthesized by the sol-gel method which have excellent flowability without agglomerating firmly. The inorganic oxide particles may be surface treated inorganic oxide particles whose surface is preferably hydrophobized.

The inventors of the present invention conducted intensive studies to attain the above object. As a result, they found that when a coagulant comprising a specific compound is added to a dispersion of inorganic oxide particles obtained by the hydrolysis and polycondensation reaction of a metal alkoxide, that is, the sol-gel method in the presence of a basic catalyst, the inorganic oxide particles can be easily collected by filtration which is a general solid-liquid separation method.

As described above, it was confirmed that the inorganic oxide particles obtained by filtration after the addition of a specific coagulant do not agglomerate firmly and are excellent in disintegration properties as compared with inorganic oxide particles taken out by a known solvent distillation-off method.

That is, the present invention is a method for producing inorganic oxide particles, comprising at least the following steps of:
- coagulating a dispersion obtained by carrying out the hydrolysis reaction and the polycondensation reaction of a metal alkoxide in the presence of a basic catalyst;
- filtering the dispersion to obtain particles; and
- drying the particles, wherein
- the step of coagulating the dispersion is carried out by adding a coagulant comprising at least one compound selected from the group consisting of carbon dioxide, ammonium carbonate, ammonium hydrogen carbonate and ammonium carbamate (to be simply referred to as "coagulant" hereinafter) to the dispersion.

Surface treated inorganic oxide particles whose surface has been hydrophobized can be produced by further carrying out at least one of the following two steps:

(1) a first surface treating step for carrying out a surface treatment by adding at least one surface treating agent selected from the group consisting of a silicone oil, a silane coupling agent and a silazane to the dispersion before the step of coagulating the dispersion; and (2) a second surface treating step for carrying out a surface treatment by adding at least one surface treating agent selected from the group consisting of a silicone oil, a silane coupling agent and a silazane to the dried inorganic oxide particles after the above drying step.

Both the above first surface treatment step and the second surface treatment step may be carried out.

BEST MODE FOR CARRYING OUT THE INVENTION

The present invention will be described in detail hereinunder.

<<Method for Producing Inorganic Oxide Particles>>

(1) Reaction of Sol-Gel Method

In the method of the present invention, first comes a reaction step for obtaining a dispersion of inorganic oxide particles dispersed in a solvent by the hydrolysis and polycondensation reaction of a metal alkoxide, that is, the reaction of the sol-gel method in the presence of a basic catalyst.

The method for producing a dispersion containing inorganic oxide particles by the sol-gel method is known, and this process can be carried out in the same manner as in the prior art even in the present invention. That is, a metal alkoxide which is a raw material is hydrolyzed and polycondensed in a suitable solvent in the presence of a suitable basic catalyst.

<Metal Alkoxide>

The metal alkoxide used in the production method of the present invention is not particularly limited if it is a compound used for the production of inorganic oxide particles by the reaction of the sol-gel method and is suitably selected according to the type of the inorganic oxide particles to be produced.

Examples of the metal alkoxide for obtaining the inorganic oxide particles which will be described hereinafter in the present invention include titanium alkoxides such as titanium tetraisopropoxide and titanium tetra-n-butoxide; zirconium alkoxides such as zirconium n-butoxide and zirconium t-butoxide; boron alkoxides such as trimethyl borate and triethyl borate; aluminum alkoxides such as aluminum n-butoxide and aluminum isopropoxide; indium alkoxides such as indium (III) isopropoxide; silicon alkoxides (alkoxysilanes) such as methyl trimethoxysilane, methyl triethoxysilane, tetramethoxysilane, tetraethoxysilane, tetraisopropoxysilane and tetrabutoxysilane; and alkoxides of the group IV elements excluding silicon such as germanium (IV) isopropoxide, germanium (IV) methoxide and tin (IV) butoxide.

Out of the above metal alkoxides, titanium tetraisopropoxide, titanium tetra-n-butoxide, zirconium n-butoxide, aluminum n-butoxide, aluminum isopropoxide, methyltrimethoxysilane, methyltriethoxysilane, tetramethoxysilane, tetraethoxysilane, tetraisopropoxysilane and tetrabutoxysilane are preferred, titanium tetraisopropoxide, zirconium n-butoxide, tetramethoxysilane and tetraethoxysilane are more preferred as they can be easily acquired industrially and are easy to handle, and methyltrimethoxysilane, tetramethoxysilane and tetraethoxysilane are particularly preferred.

In the production method of the present invention, the above metal alkoxides may be used alone or in combination of two or more. When two or more metal alkoxides are used in combination, composite inorganic oxide particles containing silica can be obtained by mixing an alkoxysilane with a metal alkoxide excluding the alkoxysilane. After silica particles having a certain diameter are obtained from the hydrolysis and polycondensation of an alkoxysilane, a metal alkoxide excluding the alkoxysilane may be added to further carry out hydrolysis and polycondensation. In this case, composite inorganic oxide particles in which another metal oxide is bonded to the surface of each silica core particle can be obtained.

When the metal alkoxide is liquid at room temperature and atmospheric pressure, it may be used as it is or after it is diluted with an organic solvent which will be described hereinafter. When the metal alkoxide is solid at room temperature and atmospheric pressure, it may be used after it is dissolved or dispersed in an organic solvent.

<Basic Catalyst>

In the production of the inorganic oxide particles by the sol-gel method, a suitable catalyst is preferably used. In the sol-gel method, an acidic catalyst may be used. In the present invention, a basic catalyst is used as it is easy to obtain spherical particles which are uniform in particle size. Although particle growth is often carried out after pre-hydrolysis in the presence of an acidic catalyst in the sol-gel method, use of the acidic catalyst for the pre-hydrolysis is not excluded and a basic catalyst should be used at the time of particle growth in the present invention.

As the basic catalyst used in the present invention, a known basic catalyst which is used for the production of inorganic oxide particles by the reaction of the sol-gel method may be preferably used.

Examples of the basic catalyst include an amine compound and an alkali metal hydroxide. The amine compound is preferably used because high-purity inorganic oxide particles which have a low total content of impurities containing a metal excluding the metal element constituting the inorganic oxide particles of interest are obtained. Examples of the amine compound include ammonia, methylamine, dimethylamine, trimethlamine, ethylamine, dimethylamine and trimethylamine. Out of these, ammonia is particularly preferably used as it is easily removed due to its high volatility and the reaction rate of the sol-gel method is high.

The above basic catalysts may be used alone or in combination of two or more.

As the above basic catalyst, an industrially available basic catalyst may be used as it is (in a commercially offered state) or after it is diluted with water or an organic solvent like ammonia water. Particularly preferably, the basic catalyst is diluted with water to control its concentration as required so as to prepare an aqueous solution as it can easily control the reaction rate. When an aqueous solution of the basic catalyst is used, its concentration is preferably 1 to 30 mass % as it is industrially easily acquired and its concentration is easily controlled.

The content of the basic catalyst may be suitably determined in consideration of the reaction rates of the hydrolysis and polycondensation reaction of the metal alkoxide. The basic catalyst is used to ensure that its content in the reaction solution becomes preferably 0.1 to 60 mass %, more preferably 0.5 to 40 mass % based on the mass of the metal alkoxide in use.

<Solvent>

The solvent used in the hydrolysis and polycondensation reaction of the above metal alkoxide in the present invention is preferably a polar solvent. The polar solvent as used herein is an organic solvent which dissolves 10 g or more of water per 100 g at room temperature and atmospheric pressure, or water. A plurality of organic solvents excluding water may be used in combination. In this case, a mixture of the organic solvents should meet the above requirement.

Examples of the organic solvent which is a polar solvent excluding water include alcohols such as methanol, ethanol, isopropyl alcohol and butanol; ethers such as diethyl ether, tetrahydrofuran and dioxane; and amide compounds such as dimethyl formamide, dimethyl acetamide and N-methylpyrrolidone.

Since an alcohol is by-produced at the time of the reaction of the sol-gel method, it is particularly preferred to use an alcohol such as methanol, ethanol, isopropyl alcohol or butanol out of these because it suppresses the inclusion of unnecessary impurities into a dispersion of the inorganic oxide particles after the reaction and can be easily removed by heating.

The above organic solvents and water may be used alone or in combination of two or more solvents.

The amount of the organic solvent or water may be suitably determined according to the particle diameters of the inorganic oxide particles of interest and the desired concentration value of the inorganic oxide particles in the inorganic oxide particle dispersion after the reaction of the sol-gel method. For example, when an alcohol is used as the organic solvent, the amount of the alcohol based on the mass (100 mass %) of the inorganic oxide particle dispersion obtained by the reaction of the sol-gel method is preferably 10 to 90 mass %, more preferably 15 to 80 mass %.

Water is indispensable for the reaction of the sol-gel method (therefore, the above polar solvent for dissolving water is used). When the above basic catalyst is added as an aqueous solution and when water is used as part or all of the solvent, water does not need to be added to the reaction solution separately. However, in other cases, water required for the sol-gel reaction must be added separately.

The amount of water is suitably adjusted and selected according to the particle diameters of the inorganic oxide particles to be produced. When the amount of water is too small, the reaction rate becomes slow and when the amount is too large, drying (removal of the solvent) takes long. Therefore, the amount of water is selected in consideration of these. The amount of water is preferably 2 to 50 mass %, more preferably 5 to 40 mass % based on the total mass of the inorganic oxide particle dispersion obtained by the reaction of the sol-gel method.

Water may be used as part or all of the reaction solvent and may be added to the reaction solution after all reaction raw materials excluding water are prepared. However, to promote the reaction of the sol-gel method swiftly and stably, it is preferred that water should be used as part of the solvent, that is, a mixture of water and an organic solvent should be used as the solvent. As for water as a solvent as used herein, a case where water is added by the addition of a basic catalyst is also included.

<Reaction Conditions>

The hydrolysis and polycondensation reaction (reaction of the sol-gel method) in the present invention are carried out in the presence of a basic catalyst as described above. Known conditions may be adopted as the reaction conditions, and the method of contacting the metal alkoxide to the basic catalyst is not particularly limited and may be suitably selected and determined in consideration of the constitution of a reactor and a reaction scale.

One example of the reaction method in the sol-gel method is given below.

Water, a polar solvent (organic solvent) excluding water and a basic catalyst are placed into a vessel, and a metal alkoxide (or an organic solvent solution of a metal alkoxide) and an aqueous solution of a basic catalyst are added to the reactor at the same time. According to this method, the vessel efficiency is high and spherical inorganic oxide particles which are uniform in particle size can be manufactured efficiently at high producibility advantageously. In this case, after part of the metal alkoxide is added, the remaining metal alkoxide and the basic catalyst may be added at the same time.

When two or more metal alkoxides are used in combination, they may be mixed together and added simultaneously, or they may be added sequentially. Particularly when a composite inorganic oxide containing silica is to be produced, the pre-hydrolysis and polycondensation reaction of one of the metal alkoxides are first carried out and then the other metal alkoxide is added to continue the reaction, thereby making it possible to produce composite metal oxide particles. For example, the hydrolysis and polycondensation reaction of an alkoxysilane in methanol in the presence of hydrochloric acid are carried out to hydrolyze the alkoxysilane with the acidic catalyst and then a metal alkoxide excluding the alkoxysilane, such as titanium tetraisopropoxide, is added to continue the reaction, thereby making it possible to produce a composite inorganic oxide having a core made of silica and a shell made of titania.

As for the addition of the metal alkoxide and the basic catalyst, they are preferably added directly into the reaction liquid a little at a time. The expression "added directly into the reaction liquid a little at a time" means that the end of a drip tube opening is immersed in the reaction liquid when the above raw material is added dropwise to the reaction liquid. The position of the end of the drip tube opening is not particularly limited if it is in the liquid but desirably a position near an agitating blade where stirring is fully carried out and droppings can be diffused into the reaction liquid swiftly.

The addition time of the metal alkoxide and the basic catalyst (a period of time from the start of addition to the end of addition) is a very important factor in the production of particles having a narrow particle size distribution. When this addition time is too short, the particle size distribution tends to become wide and when the addition time is too long, stable particle growth becomes impossible. Therefore, to obtain inorganic oxide particles having a narrow particle size distribution and uniform in particle size, an addition time suitable for particle growth must be adopted. From this point of view, the above addition time is preferably 0.2 to 8 hours per 100 nm of the desired particle diameter.

The reaction temperature is not particularly limited if it is a temperature at which the reaction of the sol-gel method proceeds swiftly and suitably selected according to the particle diameters of the inorganic oxide particles of interest. In general, as the reaction temperature becomes lower, the particle diameters of the obtained inorganic oxide particles become larger. To obtain inorganic oxide particles having a median diameter of 0.01 to 5 μm, the reaction temperature is suitably selected from a range of −10 to 60° C.

To enable the reaction of the sol-gel method to proceed without fail, after the addition of the metal alkoxide and the basic catalyst, ageing (existence of a time interval before the addition of a surface treating agent) may be carried out. In this case, the ageing temperature is preferably the same as the reaction temperature, that is, −10 to 60° C., and the ageing time is preferably 0.25 to 5 hours.

To obtain inorganic oxide particles having a desired particle diameter, a metal alkoxide and a basic catalyst may be added again after ageing to increase the particle diameters of the inorganic oxide particles.

<Dispersion of Inorganic Oxide Particles>

The dispersion obtained by the above method contains inorganic oxide particles corresponding to the element of the above metal alkoxide used as the raw material. What kind of inorganic oxide particles are obtained according to the type, amount and addition order of the metal alkoxide in use would be obvious for people having ordinary skill in the art.

Out of the inorganic oxides, silicon, titanium, zirconium or aluminum oxide and composite inorganic oxides containing two or more of these elements are preferred. Silica or a composite inorganic oxide containing silicon and another metal element is more preferred and silica is most preferred because it has high reactivity with a surface treating agent which will be described hereinafter and excellent physical properties when it is used as an external additive for toners.

Although the median diameter of the inorganic oxide particles obtained by the reaction of the sol-gel method is generally 0.01 to 5 μm, the production method of the present invention can be employed regardless of the particle diameters of the inorganic oxide particles. It is difficult to collect inorganic oxide particles having a median diameter of 1 μm or less by filtration which is generally employed by solid-liquid separation. When the method of the present invention is employed for the production of inorganic oxide particles having a median diameter of 0.01 to 1 μm, inorganic oxide particles having a small particle diameter can be easily collected advantageously.

The inorganic oxide particles produced by the reaction of the sol-gel method are characterized by a narrow particle size distribution. The inorganic oxide particles obtained by the above production method have a very narrow particle size distribution. For example, the variation coefficient as one of the indices of the width of a particle size distribution of can be set to 40% or less. In the present invention, the variation coefficient can also be set to 30% or less. However, the production method of the present invention can be employed regardless of the particle size distribution width of the inorganic oxide particles contained in the dispersion.

The inorganic oxide particles contained in the dispersion obtained by the above method are dispersed in a mixed solvent of the polar solvent in use and an alcohol produced by the hydrolysis of the metal alkoxide.

When the content of the inorganic oxide particles in the dispersion is too high, the viscosity of the dispersion becomes too high, thereby making it difficult to handle it. When the content of the inorganic oxide particles in the dispersion is too low, the amount of the inorganic oxide particles obtained by one time of the reaction becomes small, which is uneconomical. From this point of view, the content of the inorganic oxide particles in the obtained inorganic oxide particle dispersion is preferably 1 to 40 mass %, particularly preferably 2 to 25 mass %. Therefore, the amount of the polar solvent, especially the polar solvent excluding water is preferably adjusted to ensure that the content of the inorganic oxide particles falls within the above range. When the content of the inorganic oxide particles in the dispersion obtained by the reaction of the sol-gel method is too high and therefore it is difficult to handle the dispersion, it is preferred to carry out the control of the content of the inorganic oxide particles by adding the polar solvent before the surface treating step which will be described next.

(2) First Surface Treating Step

In the method for producing inorganic oxide particles, comprising the steps of coagulating the dispersion obtained as described above, filtering it to obtain particles and drying the particles, the step of coagulating the dispersion is carried out by adding a coagulant comprising at least one compound selected from the group consisting of carbon dioxide, ammonium carbonate, ammonium hydrogen carbonate and ammonium carbamate to the dispersion.

However, in the method of the present invention, before the step of coagulating the above dispersion, a surface treatment (first surface treatment) may be carried out by adding at least one surface treating agent selected from the group consisting of a silicone oil, a silane coupling agent and a silazane to the dispersion.

As the above silicone oil, known silicone oils which are generally used for the surface treatment of inorganic oxide particles may be used without restriction, and a suitable silicone oil is selected and used according to the required performance of surface treated inorganic oxide particles.

Examples of the silicone oil include dimethyl silicone oil, methyl phenyl silicone oil, methyl hydrogen silicone oil, alkyl modified silicone oil, amino modified silicone oil, epoxy modified silicone oil, carboxyl modified silicone oil, carbinol modified silicone oil, methacryl modified silicone oil, polyether modified silicone oil and fluorine modified silicone oil.

By using dimethyl silicone oil out of these, the hydrophobilization of the inorganic oxide particles can be carried out efficiently.

The amount of the silicone oil is not particularly limited but when it is too small, the surface treatment becomes unsatisfactory and when it is too large, a post-treatment becomes complicated. Therefore, the amount of the silicone oil is preferably 0.05 to 80 parts by mass, more preferably 0.1 to 60 parts by mass based on 100 parts by mass of the inorganic oxide particles in use.

As the above silane coupling agent, known silane coupling agents which are generally used for surface treatment may be used without restriction, and a suitable silane coupling agent is selected and used according to the required performance of surface treated inorganic oxide particles.

Examples of the silane coupling agent include methyl trimethoxysilane, methyltriethoxysilane, hexyltrimethoxysilane, decyltrimethoxysilane, phenyltriethoxysilane, vinyltrimethoxysilane, vinyltriethoxysilane, (3-methacryloyloxypropyl)trimethoxysilane, (3-methacryloyloxypropyl)triethoxysilane, (3-acryloyloxy)-trimethoxysilane, (3-glycidoxypropyl)trimethoxysilane, (3-glycidoxypropyl)triethoxysilane, (3-aminopropyl)-trimethoxysilane, (3-aminopropyl)triethoxysilane, [N-(2-aminoethyl)-3-aminopropyl]trimethoxysilane, [N-(2-aminoethyl)-3-aminopropylmethyl]dimethoxysilane, (N-phenyl-3-aminopropyl)trimethoxysilane, (N,N-dimethyl-3-aminopropyl) trimethoxysilane, (N,N-diethyl-3-aminopropyl) trimethoxysilane and 4-styryltrimethoxysilane.

Out of these, methyltrimethoxysilane, methyltriethoxysilane, hexyltrimethoxysilane and decyl trimethoxysilane are preferred because the hydrophobization of the inorganic oxide particles can be carried out efficiently.

The amount of the silane coupling agent is not particularly limited but when it is too small, the surface treatment becomes unsatisfactory and when it is too large, the post-treatment becomes complicated. Therefore, the amount of the silane coupling agent is preferably 0.05 to 80 parts by mass, more preferably 0.1 to 40 parts by mass based on 100 parts by mass of the inorganic oxide particles in use.

As the above silazane, known silazanes which are generally used for surface treatment may be used without restriction. Out of the silazanes, hexamethylsilazane is preferred because it is highly reactive and easy to handle.

The amount of the silazane is not particularly limited but when it is too small, the surface treatment becomes unsatisfactory and when it is too large, the post-treatment becomes complicated. Therefore, the amount of the silazane is preferably 0.1 to 150 parts by mass, more preferably 1 to 120 parts by mass based on 100 parts by mass of the inorganic oxide particles in use.

The above surface treating agents may be used alone or in combination of two or more.

Out of the above surface treating agents, at least one selected from the group consisting of a silane coupling agent and a silazane is preferably used, and a silazane is more preferably used as the flowability of the obtained surface treated inorganic oxide particles becomes high.

The method of adding the surface treating agent is not particularly limited. When the surface treating agent is a low-viscosity liquid at room temperature and atmospheric pressure, it may be added dropwise to the dispersion or sprayed upon the dispersion. Preferably, it is added dropwise to the dispersion because the operation is easy. When the surface treating agent is a high-viscosity liquid or solid, it is added to a suitable organic solvent to prepare a solution or a dispersion which is then added in the same manner as the low-viscosity liquid. The organic solvent used herein is the same as the above polar solvent. Further, when the surface treating agent is gaseous, it is blown into the dispersion to become fine bubbles.

The treating temperature for the first surface treatment may be determined in consideration of the reactivity of the surface treating agent in use. However, when the treating temperature is too low, the proceeding of the reaction becomes slow and when the treating temperature is too high, the operation becomes troublesome. Therefore, the treating temperature is preferably 10 to 100° C., more preferably 20 to 80° C.

The treating time for the first surface treatment is not particularly limited and may be determined in consideration of the reactivity of the surface treating agent in use. In consideration of the complete proceeding of the surface treating reaction and the reduction of the process time, the treating time is preferably 0.1 to 48 hours, more preferably 0.5 to 24 hours.

(3) Coagulation Step

In the method of the present invention, the coagulation of the dispersion obtained as described above is carried out without the above first surface treatment (2) or after the first surface treatment (2).

This coagulation step is carried out by adding a coagulant comprising at least one compound selected from the group consisting of carbon dioxide, ammonium carbonate, ammonium hydrogen carbonate and ammonium carbamate to the dispersion. By adding the above coagulant to the dispersion, a weak agglomerate of the inorganic oxide particles is formed in the dispersion. This agglomerate can be existent stably in the dispersion due to the existence of the coagulant or a derivative thereof in the dispersion and therefore can be easily collected by filtration.

A technology for forming an agglomerate of inorganic oxide particles by adding a metal salt to a dispersion of the inorganic oxide particles is known. According to this method, when a sodium salt or a potassium salt is used, it is possible that a metal element component constituting the salt is contained in the obtained inorganic oxide particles, thereby requiring a cleaning (purification) operation for removing this, which is industrially disadvantageous.

In contrast to this, as the above coagulant used in the present invention is easily decomposed and removed by slight heating, high-purity inorganic oxide particles can be easily produced. According to the method of the present invention, the content of elemental sodium in the obtained inorganic oxide particles can be reduced to 100 ppm or less, preferably 10 ppm or less.

The amount and the addition method of the coagulant may be set as follows according to the type of the coagulant in use. The amount of the coagulant is set in consideration of balance between the degree of forming a weak agglomerate of inorganic oxide particles in the dispersion and the pointlessness of using an unduly large amount of the raw material. The mass of the inorganic oxide particles which is the basis of the amount of the coagulant below is a value based on the supposition that all the metal alkoxide in use is hydrolyzed and polycondensed to become inorganic oxide particles.

In the case of any coagulant, the preferred amount of the coagulant when both the above first surface treatment and the second surface treatment which will be described hereinafter are not carried out differs from the amount of the coagulant when at least one of the surface treatments is carried out.

When carbon dioxide is used as the above coagulant, the amount thereof is preferably 0.005 part or more by mass, more preferably 0.005 to 300 parts by mass based on 100 parts by mass of the inorganic oxide particles contained in the dispersion. When no surface treatment is carried out on the inorganic oxide particles, the amount of carbon dioxide is preferably 0.05 part or more by mass, more preferably 0.05 to 300 parts by weight, particularly preferably 0.25 to 200 parts by mass based on 100 parts by mass of the inorganic oxide particles. When the surface treatment is carried out on the inorganic oxide particles, the amount of carbon dioxide is preferably 15 parts or more by mass, more preferably 15 to 300 parts by mass, particularly preferably 17 to 200 parts by mass based on 100 parts by mass of the inorganic oxide particles.

Examples of the method of adding carbon dioxide include one in which carbon dioxide in a gaseous state is blown into the dispersion and one in which carbon dioxide in a solid state (dry ice) is added. Out of these, the latter method in which carbon dioxide in a solid state is added is preferred as the operation is simple.

When ammonium carbonate, ammonium hydrogen carbonate or ammonium carbamate is used as the above coagulant, the amount thereof is preferably 0.001 part or more by mass, more preferably 0.001 to 80 parts by mass based on 100 parts by mass of the inorganic oxide particles contained in the dispersion. When no surface treatment is carried out on the inorganic oxide particles, the amount of ammonium carbonate, ammonium hydrogen carbonate or ammonium carbamate is preferably is 0.001 to 15 parts by mass, particularly preferably 0.001 to 10 parts by mass based on 100 parts by mass of the inorganic oxide particles. When the surface treatment is carried out on the inorganic oxide particles, the amount of ammonium carbonate, ammonium hydrogen carbonate or ammonium carbamate is preferably 15 parts or more by mass, more preferably 15 to 80 parts by mass, much more preferably 17 to 60 parts by mass, particularly preferably 20 to 50 parts by mass based on 100 parts by mass of the inorganic oxide particles.

Ammonium carbonate, ammonium hydrogen carbonate or ammonium carbamate may be added in a solid state or dissolved in a suitable solvent to be added as a solution. The solvent which is used to add the above coagulant as a solution is not particularly limited if it dissolve the coagulant. However, water is preferably used as it has high dissolution ability and is easily removed after filtration. The concentration of a solution of ammonium carbonate, ammonium hydrogen carbonate or ammonium carbamate is not particularly limited if the coagulant is dissolved. However, when the concentration is too low, the amount of the solution becomes large, which is uneconomical. Therefore, the concentration is preferably 2 to 15 mass %, particularly preferably 5 to 12 mass %.

The above coagulants may be used alone or in combination of two or more.

A mixture of ammonium hydrogen carbonate and ammonium carbamate, which is marketed as so-called "ammonium carbonate", may be used as it is or after it is dissolved in a suitable solvent. The total amount of ammonium hydrogen carbonate and ammonium carbamate, the type of the solvent used to add these as a solution and the concentration of the solution are the same as those in the case of ammonium carbonate, ammonium hydrogen carbonate or ammonium carbamate.

The coagulant in the present invention is preferably at least one selected from the group consisting of ammonium hydrogen carbonate and ammonium carbamate, more preferably ammonium hydrogen carbonate, particularly preferably an aqueous solution of ammonium hydrogen carbonate.

pH of the inorganic oxide particle dispersion when the coagulant is added is desirably selected from a range which ensures that the coagulant does not cause unpreferred decomposition in the dispersion and the effect of the present invention can be obtained effectively. From this point of view, pH of the dispersion is set to preferably an alkaline range, more preferably 9 or more.

The temperature of the inorganic oxide particle dispersion when the coagulant is added is desirably set to ensure that a weak agglomerate of the inorganic oxide particles formed by the addition of the coagulant can be existent stably. From this point of view, the temperature of the dispersion is preferably −10 to 60° C. which is the same as the reaction temperature of the sol-gel method, more preferably 10 to 40° C.

After the addition of the coagulant, it is preferred that ageing should be carried out, that is, a time interval should exist before the subsequent filtration step. By carrying out ageing after the addition of the coagulant, the formation of the above weak agglomerate of the inorganic oxide particles is promoted advantageously. Although a longer ageing time is better, a too long ageing time is uneconomical. When the ageing time is too short, the formation of a weak agglomerate of the inorganic oxide particles becomes unsatisfactory. The ageing time is preferably 0.5 to 72 hours, particularly preferably 1 to 48 hours. The temperature of the dispersion at the time of ageing is not particularly limited and may be within the same temperature range as that for adding the coagulant. The same temperature as that for adding the coagulant suffices.

(4) Filtration Step

In the method of the present invention, next comes the step of collecting the inorganic oxide particles by filtration from the dispersion obtained by adding the coagulant preferably after ageing is carried out as described above.

The inorganic oxide particles which form a weak agglomerate by adding the above coagulant can be easily collected by filtration. The filtration method is not particularly limited and a known method such as vacuum filtration, pressure filtration or centrifugal filtration may be employed.

A filter paper, a filter or a filter cloth (to be generically referred to as "filter paper or the like" hereinafter) used for filtration may be used without restriction if they can be industrially acquired and suitably selected according to the scale of a separation apparatus (filtering mechanism). According to the present invention, since a weak agglomerate of primary particles is formed by adding the coagulant, the opening size of the filter paper or the like should be much larger than the primary particle diameter. For example, when the inorganic oxide particles have a median diameter of 0.01 to 5 μm, a filter paper or the like having an opening size of about 5 μm suffices. Since a filter paper or the like having a large opening size can be used, the inorganic oxide particles can be filtered quickly.

The inorganic oxide particles are collected as a cake by filtration.

When an aqueous solution of ammonium hydrogen carbonate is used as the coagulant in the above coagulating step (3), the solvent, the basic catalyst and the unreacted surface treating agent used in the reaction of the sol-gel method can be decomposed or removed by rinsing the obtained cake with a suitable solvent such as water or an alcohol.

(5) Drying Step

Then, the inorganic oxide particles collected by the above filtering step (4) are dried in this step.

In the present invention, when the cake of the inorganic oxide particles collected as described above is dried at a temperature of 35° C. or higher, its disintegration properties are further improved. Therefore, the drying temperature in the drying step of the present invention is preferably 35° C. or higher. By heating at this temperature, the coagulant remaining in the cake without being removed by the above filtration and rinsing can be easily removed by thermal decomposition. This is also one of the big advantages of the present invention.

The drying method is not particularly limited and a known method such as air drying or drying under reduced pressure may be employed. However, since it was made clear by studies conducted by the inventors of the present invention that the inorganic oxide particles are more easily disintegrated when they are dried under reduced pressure than when they are dried under atmospheric pressure, it is preferred to employ drying under reduced pressure.

A higher drying temperature is more advantageous from the viewpoint of the decomposition efficiency of the coagulant and the acquisition of inorganic oxide particles which are easily disintegrated. However, when the drying temperature is too high, the substituent introduced into the surfaces of the inorganic oxide particles by the surface treatment is decomposed disadvantageously. Further, when the drying temperature is too high, the content of water on the surfaces of the inorganic oxide particles becomes too low, wherein when the obtained inorganic oxide particles are used as an external additive for toners, the rate of charge rise drops disadvantageously. Therefore, to balance between them, the drying temperature is preferably 35 to 200° C., more preferably 50 to 200° C., much more preferably 80 to 200° C., particularly preferably 120 to 200° C.

Although the drying time is not particularly limited, when it is 2 to 48 hours, the inorganic oxide particles can be completely dried.

(6) Second Surface Treating Step

In the method of the present invention, a surface treatment (second surface treatment) may be carried out by further adding at least one surface treating agent selected from the group consisting of a silicone oil, a silane coupling agent and a silazane to the inorganic oxide particles obtained as described above.

The surface treating agent which can be used in this step may be the same as those explained as the surface treating agent for carrying out the above first surface treatment. However, in this second surface treating step, it is preferred to use a surface treating agent which can be chemically bonded to a functional group on the surfaces of the inorganic oxide particles directly since the obtained surface treated oxide particles have excellent flowability as compared with a case where a surface treating agent having no reactivity (for example, an ordinary silicone oil) is used.

The amount of the surface treating agent in the second surface treatment step is as follows according to its type.
Silicone oil: preferably 0.01 to 50 parts by mass, more preferably 0.01 to 20 parts by mass based on 100 parts by mass of the inorganic oxide particles after the first surface treatment;
Silane coupling agent: preferably 0.01 to 100 parts by mass, more preferably 0.2 to 50 parts by mass based on 100 parts by mass of the inorganic oxide particles after the first surface treatment; and
Silazane: preferably 0.10 to 150 parts by mass, more preferably 0.2 to 100 parts by mass based on 100 parts by mass of the inorganic oxide particles after the first surface treatment.

The second surface treatment in this step is preferably carried out in a so-called "dry process". That is, the above surface treating agent is added to the inorganic oxide particles obtained through the drying step and stirred by a suitable method. The method of adding the surface treating agent to the oxide particles may be suitably determined according to the form of the surface treating agent in use. For example, when the surface treating agent is a low-viscosity liquid at a process temperature and a process pressure, it may be added dropwise to the inorganic oxide particles or sprayed upon the inorganic oxide particles. When the surface treating agent is a high-viscosity liquid or solid, it may be added in the same manner as the low-viscosity liquid after it is diluted with a small amount of a suitable organic solvent. Examples of the organic solvent used herein are the same as the polar solvents explained in (1) Reaction of the sol-gel method. Further, when the surface treating agent is gaseous, the inorganic oxide particles and the surface treating agent are stirred while they are kept airtight in a vessel.

The second surface treatment in this step is preferably carried out in the presence of water in order to keep a sufficient amount of a silanol group which can react with the surface treating agent on the surfaces of the inorganic oxide particles. In this case, the amount of water is preferably 30 parts or less by mass, more preferably 0.2 to 20 parts by mass based on 100 parts by mass of the inorganic oxide particle.

The preferred treating conditions when the second surface treating step is carried out are as follows.
Treating temperature: preferably 100 to 500° C., more preferably 150 to 350° C.;
Treating pressure: preferably $3\times10^5$ or less, more preferably $1\times10^4$ to $2\times10^5$ Pa; and
Treating time: preferably 1 to 300 minutes, more preferably 5 to 180 minutes.

The second surface treatment in this step may be carried out once or two or more times. When the second surface treatment is carried out two or more times, the types and amounts of the surface treating agents in use and treating conditions may be the same or different each time. Particularly when a different surface treating agent is used each time, surface treated oxide particles having finely controlled surface properties can be obtained.

<<Inorganic Oxide Particles>>

The inorganic oxide particles of the present invention produced as described above have excellent flowability. The surface treated inorganic oxide particles obtained by the method of the present invention have a very low total content of impurities such as nitrogen. To further improve the flowability of the inorganic oxide particles of the present invention, it is preferred that at least one of the first surface treatment step (2) and the second surface treatment step (6) should be carried out, and it is more preferred that both of them should be carried out.

The flowability of the surface treated inorganic oxide particles can be evaluated as agglomeration degree and as this value becomes smaller, the flowability becomes higher.

This agglomeration degree can be calculated as follows. After a sieve having an opening of 355 μm, a sieve having an opening of 250 μm and a sieve having an opening of 150 μm (all of them are sieves having a diameter of 75 mm based on JIS Z8801) are placed one upon another in this order from the top at fixed intervals (2 cm), 5 g of the particles is put on the top sieve, and these sieves are vibrated vertically at an amplitude of 1 mm and a frequency of 60 Hz for 15 seconds, the amounts of the remaining particles on these sieves are measured and inserted into the following equation.

Agglomeration degree(%)={(amount of remaining particles on top sieve+amount of remaining particles on middle sieve×0.6+amount of remaining particles on bottom sieve×0.2}÷initial mass of surface treated inorganic oxide particles×100

This agglomeration degree can be easily measured by using a commercially available particulate characteristic measuring instrument, for example, the Powder Tester (registered trademark) of Hosokawa Micron Corporation.

When the inorganic oxide particles obtained by the method of the present invention are subjected to at least one of the first surface treatment and the second surface treatment, the agglomeration degree thereof can be set to 60% or less or further to 50% or less.

The nitrogen content of the inorganic oxide particles can be determined by a method in which the oxide particles are completely oxidized at a high temperature and elemental analysis is made on the particles.

The nitrogen content of the inorganic oxide particles obtained by the method of the present invention can be set to 0.05% or less or further to 0.02% or less.

Since the surface treated inorganic oxide particles obtained by the method of the present invention have excellent flowability as described above, preferably, the surface thereof is highly hydrophobized, they can be advantageously used as an external additive for toners or an external additive for coating materials.

When the surface treated inorganic oxide particles obtained by the method of the present invention are used as an external additive for toners, as the surface treated inorganic oxide particles have excellent flowability, they can increase the surface overage of resin particles for toners. Since the surface treated inorganic oxide particles obtained by the preferred method of the present invention are highly hydrophobized and the adsorption and dissociation of water on the surface which causes the leakage of toner charge hardly occur, charge stability is high. Since water is existent on the surfaces of the particles, the rate of charge rise becomes high advantageously. Since inorganic oxide particles produced by the conventional sol-gel method contain a significant amount of water capable of adsorption and dissociation, when they are used as an external additive for toners, the leakage of toner charge readily occurs, whereby charge stability degrades.

Since the surface treated inorganic oxide particles obtained by the method of the present invention have hydrophobic nature, they can be advantageously used as an additive for resin materials such as epoxy resin and acrylic resin.

Further, since the inorganic oxide particles obtained by the method of the present invention have extremely high purity, when they are used as a sealant for semiconductors or an external additive for toners, they can be advantageously used without contaminating a material of interest.

EXAMPLES

The following examples and comparative examples are provided for the purpose of further illustrating the present invention but are in no way to be taken as limiting. The methods of measuring physical properties in the present invention are as follows.

(1) Measurement of Median Diameter of Inorganic Oxide Particles Contained in Dispersion The median diameter of the inorganic oxide particles contained in the dispersion was measured by an image analyzing method using a scanning electron microscope (to be referred to as "SEM" hereinafter).

The dispersion of the inorganic oxide particles obtained after the end of the sol-gel reaction was diluted with pure water and the diluted dispersion was dropped on a silicon wafer. Thereafter, it was dried under reduced pressure at room temperature for 2 or more hours to remove the dispersion medium, and the obtained product was used as a sample for SEM observation. The median diameter of the formed sample was obtained by observing the formed sample through SEM several times by changing the imaging site and converting the calculated value as the particle diameter $D_{50}$ of 200 or more inorganic oxide particles into a volume-based value.

(2) Measurement of Median Diameter and Variation Coefficient of Inorganic Oxide Particles The median diameter of the inorganic oxide particles finally obtained in each example was measured by the following laser diffraction scattering method.

The inorganic oxide particles obtained in each example were pounded in a mortar, 0.1 g of the pounded particles was collected and placed into a glass bottle having an inner diameter of 4 cm and a height of 11 cm, and 50 g of pure water was placed into the glass bottle in Examples 1-1 to 1-11, Comparative Examples 1-1 and 2-1 and Reference Examples 1-2, 1-2 and 2-1 whereas 50 g of ethanol was placed into the glass bottle in Examples 2-1 to 2-19. A part 4.5 cm from the end of a probe (the inner diameter of the end: 7 mm) was immersed in this, and ultraviolet waves were applied at an output of 50 W and 40 kHz for 30 minutes to disperse the particles.

The median diameter and the variation coefficient of the obtained dispersion were measured by polarization scattering intensity difference metering using the Coulter LS230 (trade name) of Beckman Coulter Inc. at a range of 0.04 to 2000 µm. The variation coefficient was calculated from the following equation.

Variation coefficient(%)=standard deviation of particle diameters(µm)/number average value of particle diameters(µm)

As the variation coefficient become smaller, the particle size distribution becomes narrower.

(3) Measurement of Crush Strength

The inorganic oxide particles obtained in each example were put through a sieve having an opening of 1.4 mm and then through a sieve having an opening of 0.71 mm to measure inorganic oxide particles remaining on the sieve having an opening of 0.71 mm.

The inorganic oxide particles remaining on the sieve having an opening of 0.71 mm were put on an even balance, and load was applied to the inorganic oxide particles by a metal spatula to measure load when the particles were disintegrated. The measurement was carried out 50 times and the average value of 40 measurement data excluding five largest values and five smallest values was taken as a crush strength value.

As this crush strength value becomes smaller, the particles are more easily disintegrated.

(4) Measurement of Hydrophobicity 0.2 g of the inorganic oxide particles obtained in each example was added to 50 mL of water in a beaker having a capacity of 250 mL and stirred by means of a magnetic stirrer. Methanol was added to the resulting dispersion by using a burette so as to carry out titration with a point of time when the whole amount of the sample powders got wet and suspended in the solvent in the beaker as an end point. At this point, methanol was guided into the liquid through a tube so that it did not come into direct contact with the sample particles.

The volume percentage (%) of methanol in the methanol-water mixed solvent at the end point was taken as hydrophobicity.

(5) Measurement of Agglomeration Degree

A sieve having an opening of 355 µm, a sieve having an opening of 250 µm and a sieve having an opening of 150 µm were set in upper, middle and bottom stages of the PT-R Powder Tester (trade name) of Hosokawa Micron Corporation at intervals of 2 cm. After 5 g of the inorganic oxide particles was put on the sieve in the upper stage and vibrated vertically at an amplitude of 1 mm and a frequency of 60 Hz for 15 seconds, the agglomeration degree (%) was calculated from the amounts of the inorganic oxide particles remaining on the sieves based on the following equation. As the agglomeration degree becomes lower, the flowability of the inorganic oxide particles becomes higher.

Agglomeration degree(%)={(amount of remaining particles on top sieve+amount of remaining particles on middle sieve×0.6+amount of remaining particles on bottom sieve×0.2)÷5 (g)}×100

(6) Measurement of Nitrogen Content

After 50 mg of silica particles was weighed and collected on a boat by using the NC-22F high-sensitivity N.C. analyzer of Sumika Chemical Analysis Service, Ltd. and completely oxidized at 830° C., the quantitative analysis of a nitrogen component was carried out by TCD gas chromatography so as to measure the nitrogen content (mass %) of the inorganic oxide particles.

(7) Measurement of Amount of Metal Element Component

About 2 g of the inorganic oxide particles obtained in each example, comparative example or reference example was weighed precisely and transferred to a platinum dish, and 10 mL of concentrated nitric acid and 10 mL of fluoric acid were added to this in this order. The resulting dispersion was put on a hot plate set to 200° C. to be heated so as to dry up the content. After the dried product was cooled to room temperature, 2 mL of concentrated nitric acid was further added, and the resulting product was put on a hot plate set to 200° C. to be heated and dissolved. After the obtained solution was cooled to room temperature, the solution which was the content of the platinum dish was transferred to a measuring flask having a capacity of 50 mL and diluted with super pure water up to a gauge line.

This sample was used to measure the amount of the metal element component by means of an ICP emission spectrometer (ICPS-1000V of Shimadzu Corporation).

(8) Measurement of Coverage of Resin Surface 0.8 g of the inorganic oxide particles obtained in each example, comparative example or reference example and 20 g of styrene-acrylic resin particles having a medium diameter of 6.1 µm were placed into a 100 mL polyethylene bottle and mixed together by means of a shaking apparatus for 60 minutes. 50 different view fields of the obtained mixed particles were observed through an field-emission-type scanning electron microscope (S-5500 of Hitachi High-Technologies Corporation) at a magnification of 10,000×. The obtained images were used to calculate the average value of the coverage of the resin surfaces from the following equation by using an image analyzing system (IP-1000PC of Asahi Kasei Corporation). As the surface coverage becomes higher, the inorganic oxide particles are better as an external additive for toners. When this value is 5% or more, it can be evaluated as a practical level.

Surface coverage(%)=area of part covered with inorganic oxide particles/area of styrene-acrylic resin particle×100

(9) Measurement of Triboelectric Charge Quantity

Seven 50 mL screw tubular bottles were prepared, and 1 g of the mixed particles of the inorganic oxide particles and the styrene-acrylic resin used for the measurement of the coverage of the above resin surface and 99 g of a ferrite carrier having a particle diameter of 45 to 75 µm were placed into these bottles and left to stand at 25° C. and 50% RH for 24 hours or more to control their humidities. Each of the screw tubular bottles filled with the sample after humidity control was set in the VMR-5 mix rotor of As One Corporation at a rotor revolution of 90 rpm to mix them together for 1 minute, 3 minutes, 5 minutes, 10 minutes, 30 minutes, 60 minutes or 120 minutes.

The frictional charge quantity of each of the above samples was measured by means of the TB-203 powder charge quantity measurement instrument of Kyocera Chemical Corporation after nitrogen was blown into the sample at a blow pressure of 10 kPa and a pull pressure of −5 kPa.

The frictional charge quantity of the sample after 3 minutes of mixing was used as an index of the rate of charge rise. As this value becomes larger, toner characteristic properties become better.

The maximum value of the frictional charge quantity is taken as saturation frictional charge quantity, and charge stability was calculated from the following equation. As this charge stability becomes higher, toner characteristic properties become better.

Charge stability(%)=frictional charge quantity after 120 minutes of mixing(µC/g)/saturation frictional charge quantity(µC/g)×100

Production of Inorganic Oxide Particles which are not Surface Treated

Example 1-1

A dispersion of inorganic oxide particles was first prepared by the reaction of the sol-gel method. 150 g of 15 mass % ammonia water (1.2 mass % of ammonia based on the mass of a metal alkoxide which will be described hereinafter) as a basic catalyst and 1,040 g of methanol (27 mass % based on the mass of the obtained dispersion) as an organic solvent were placed into a 10-L four-necked flask and stirred at 35° C.

1,940 g of tetramethoxysilane as a metal alkoxide and 700 g of 5 mass % ammonia water (1.8 mass % of ammonia based on the mass of the metal alkoxide, a total of 3.0 mass % including ammonia contained in the ammonia water placed previously) as a basic catalyst were each independently added directly into the resulting dispersion a little at a time. The addition speed was controlled to ensure that the addition ended in 5 hours. During the sol-gel reaction, the temperature was kept at 35° C. The mass of the dispersion obtained by the above recipe was 3,830 g and the concentration of silica in the dispersion was 20 mass % (766 g of silica).

10 minutes after the start of addition, the reaction liquid was clouded, thereby confirming the proceeding of the reaction. After the end of addition, ageing was carried out for 0.5 hour.

20 g of solid carbon dioxide (dry ice) (2.6 mass % based on silica contained in the dispersion) was added as a coagulant to the obtained dispersion and left to stand for 20 hours. After 20 hours, silica particles settled out.

The dispersion after the sedimentation of the above silica particles was filtered under reduced pressure by using a quantitative filter paper (hold particle diameter of 7 µm) to obtain 1,303 g of a cake (concentrate) having a silica concentration of 57 mass %. At this point, the filtrate was transparent and a filtration leak was not confirmed. The above cake was vacuum dried at 100° C. for 16 hours to obtain 804 g of silica particles. When infrared spectroscopic (IR) analysis was made on the silica particles, no peak based on carbonic acid was detected, whereby it was confirmed that no ammonium carbonate remained.

Subsequently, the silica particles were calcined at 900° C. in air for 10 hours. 743 g of silica particles which seemed to be not sintered were obtained.

Various measurements were made on the dispersion and the silica particles in this example in accordance with the above methods. The measurement results are shown in Table 1-1.

Example 1-2

The operation of Example 1-1 was repeated except that 20 g of ammonium hydrogen carbonate (2.6 mass % based on silica contained in the dispersion) in a solid state was used as a coagulant in place of the dry ice. Various measurements were made on the dispersion and the silica particles in this example in accordance with the above methods. The measurement results are shown in Table 1-1.

Example 1-3

The operation of Example 1-1 was repeated except that the amount of the dry ice as a coagulant was changed to 200 g (26 mass % based on silica contained in the dispersion). Various measurements were made on the dispersion and the silica particles in this example in accordance with the above methods. The measurement results are shown in Table 1-1.

Example 1-4

The operation of Example 1-1 was repeated except that the ageing time after the addition of the dry ice was changed to 2 hours. Various measurements were made on the dispersion and the silica particles in this example in accordance with the above methods. The measurement results are shown in Table 1-1.

Example 1-5

The operation of Example 1-1 was repeated except that the reaction temperature of the sol-gel reaction was changed to 15° C. Various measurements were made on the dispersion and the silica particles in this example in accordance with the above methods. The measurement results are shown in Table 1-1.

Example 1-6

A dispersion of inorganic oxide particles was first prepared by the reaction of the sol-gel method. 210 g of 25 mass % ammonia water (3.1 mass % of ammonia based on the mass of a metal alkoxide which will be described hereinafter) as a basic catalyst and 310 g of methanol and 710 g of isopropanol (26.8 mass % based on the mass of the obtained dispersion) as organic solvents were placed into a 10-L four-necked flask and stirred at 40° C.

10 minutes after 26 g of tetramethoxysilane as a metal alkoxide was added dropwise to the resulting dispersion, the reaction liquid was clouded, thereby confirming the proceeding of the reaction. Subsequently, a solution consisting of 1,650 g of tetramethoxysilane as a metal alkoxide and 170 g of methanol as an organic solvent (4.5 mass % based on the mass of the obtained dispersion, a total of 31 mass % including the organic solvents placed previously) and 730 g of 25 mass % ammonia water (10.9 mass % of ammonia based on the mass of the metal alkoxide, a total of 14 mass % including ammonia contained in the ammonia water placed previously) as a basic catalyst were each independently added directly into the resulting liquid a little at a time. The addition speed was controlled to ensure that the addition ended in 2 hours. During the sol-gel reaction, the temperature was kept at 40° C. The mass of the dispersion obtained by the above recipe was 3,806 g.

20 g of solid carbon dioxide (dry ice) (3.0 mass % based on silica contained in the dispersion) was added as a coagulant to the obtained dispersion and left to stand for 20 hours. After 20 hours, silica particles settled out.

The dispersion after the sedimentation of the above silica particles was filtered under reduced pressure by using a quantitative filter paper having a hold particle diameter of 7 μm to obtain 1,448 g of a cake (concentrate) having a silica concentration of 52 mass %. At this point, the filtrate was transparent and a filtration leak was not confirmed. The above cake was vacuum dried at 100° C. for 16 hours to obtain 807 g of silica particles. Subsequently, the silica particles were calcined at 900° C. in air for 10 hours to obtain 753 g of silica particles which seemed to be not sintered.

Various measurements were made on the dispersion and the silica particles in this example in accordance with the above methods. The measurement results are shown in Table 1-1.

Example 1-7

The operation of Example 1-6 was repeated except that pressure filtration was carried out at a pressure of 0.1 MPa by using a filter paper having an opening size of 6 μm in place of filtration under reduced pressure using a quantitative filter paper having a hold particle diameter of 7 μm. Various measurements were made on the dispersion and the silica particles in this example in accordance with the above methods. The measurement results are shown in Table 1-1.

Example 1-8

The operation of Example 1-6 was repeated except that centrifugal filtration was carried out at a revolution of 1,000 rpm by using a laminate consisting of a filter cloth having a draft quantity of 0.2 cc/(cm$^2$·sec) and a filter paper having an opening size of 6 μm in place of filtration under reduced pressure using a quantitative filter paper having a hold particle diameter of 7 μm. Various measurements were made on the dispersion and the silica particles in this example in accordance with the above methods. The measurement results are shown in Table 1-1.

Example 1-9

A dispersion of inorganic oxide particles was first prepared by the reaction of the sol-gel method. 475 g of tetramethoxysilane as a metal alkoxide was placed into a 3-L four-necked flask, and 238 g of methanol (11 mass % based on the mass of the obtained dispersion) as an organic solvent and 56 g of 0.035 mass % hydrochloric acid (0.003 mass % of hydrogen chloride based on the mass of the metal alkoxide) as an acid catalyst were added to the dispersion and stirred at room temperature for 10 minutes to hydrolyze tetramethoxysilane. Subsequently, a solution prepared by dissolving 250 g of titanium tetraisopropoxide as a metal alkoxide in 500 g of isopropanol (23 mass % based on the mass of the obtained dispersion) was added to obtain a transparent composite alkoxide solution.

256 g of isopropanol (12 mass % based on the mass of the obtained dispersion, a total of 46 mass % including methanol and isopropanol contained in the above composite alkoxide solution) and 64 g of 25 mass % ammonia water (2.2 mass % of ammonia based on the mass of the metal alkoxide) were placed into a 5-L four-necked flask and stirred while the temperature was kept at 40° C. The above alkoxide solution and 344 g of 25 mass % ammonia water (3.9 mass % of ammonia based on the mass of the metal alkoxide, a total of 6 mass % including the above) were each independently added directly into the resulting liquid a little at a time. The addition speed was controlled to ensure that the addition ended in 5 hours. 10 minutes after the start of addition, the reaction liquid was clouded, thereby confirming the proceeding of the reaction. After the end of addition, ageing was carried out for 0.5 hour. The mass of the dispersion obtained by the above recipe was 2,183 g.

Then, 150 g of solid carbon dioxide (dry ice) (58 mass % based on the composite oxide particles contained in the dispersion) as a coagulant was added to the obtained dispersion and left to stand for 4 hours. After 4 hours, silica-titania composite oxide particles settled out.

The dispersion after the sedimentation of the above particles was filtered under reduced pressure by using a quantitative filter paper (hold particle diameter of 5 μm) to obtain 398 g of a cake (concentrate) having a silica-titania composite oxide concentration of 62 mass %. At this point, the filtrate was transparent and a filtration leak was not confirmed. The above cake was vacuum dried at 100° C. for 16 hours to obtain 260 g of silica-titania composite oxide particles. Further, the silica-titania composite oxide particles were calcined at 1,050° C. in air for 12 hours to obtain 247 g of silica-titania composite oxide particles which seemed to be not sintered.

Various measurements were made on the dispersion and the silica-titania composite oxide particles in this example in accordance with the above methods. The measurement results are shown in Table 1-1.

Example 1-10

A dispersion of inorganic oxide particles was first prepared by the reaction of the sol-gel method. 4.0 g of 0.1 mass % hydrochloric acid (0.001 mass % of hydrogen chloride based on the mass of a metal alkoxide which will be described hereinafter) as an acid catalyst, 158 g of tetraethoxysilane as a metal alkoxide and 950 g of methanol (24 mass % based on the mass of the obtained dispersion) as an organic solvent were placed into a 3-L four-necked flask to carry out hydrolysis at room temperature for 2 hours under agitation. A solution prepared by dissolving 38 g of zirconium n-butoxide as a metal alkoxide in 400 g of isopropanol (10 mass % based on the mass of the inorganic oxide particle dispersion) was added to the obtained dispersion so as to prepare a composite alkoxide solution.

1,980 g of methanol (51 mass % based on the mass of the obtained dispersion) and 125 g of 25 mass % ammonia water (9.5 mass % based on the mass of the metal alkoxide) were added to a 10-L four-necked flask. When a solution prepared by dissolving 4.0 g of tetraethoxysilane as a metal alkoxide in 80 g of methanol (2 mass % based on the mass of the obtained dispersion) was added to this liquid over 5 minutes while this solution was maintained at 20° C., it was confirmed that the reaction liquid was slightly clouded.

The above composite alkoxide solution was added dropwise to this reaction liquid over 2 hours. Further, a solution prepared by dissolving 128 g of tetraethoxysilane as a metal alkoxide in 400 g of methanol (1 mass % based on the mass of the obtained dispersion, a total of 88 mass % of the organic solvents) was added dropwise over 2 hours, and ageing was carried out for 0.5 hour after the end of addition. The mass of the dispersion obtained by the above injection was 4,267 g.

20 g of solid carbon dioxide (dry ice) (21 mass % based on the composite oxide particles contained in the dispersion) as a coagulant was added to the obtained dispersion and left to stand for 20 hours. After 20 hours, silica-zirconia composite oxide particles settled out.

The dispersion after the sedimentation of the above particles was filtered under reduced pressure by using a quantitative filter paper (hold particle diameter of 5 μm) to obtain 153 g of a cake (concentrate) having a silica-zirconia composite oxide concentration of 58 mass %. This cake was vacuum dried at 100° C. for 16 hours to obtain 98 g of silica-zirconia composite oxide. Further, the silica-zirconia composite oxide was calcined at 1,000° C. in air for 6 hours to obtain 89 g of silica-zirconia composite oxide particles which seemed to be not sintered.

Various measurements were made on the dispersion and the silica-zirconia composite oxide particles in this example in accordance with the above methods. The measurement results are shown in Table 1-1.

Example 1-11

The operation of Example 1-1 was repeated except that a mixed solvent consisting of 780 g of methanol and 260 g of isopropyl alcohol was used as an organic solvent in the reaction of the sol-gel method in place of 1,040 g of methanol. Various measurements were made on the dispersion and the silica particles in this example in accordance with the above methods The measurement results are shown in Table 1-1.

Example 1-12

The operation of Example 1 was repeated except that 20 g of ammonium carbonate (2.6 mass % based on inorganic oxide particles contained in the dispersion) was used in place of the dry ice. Various measurements were made on the dispersion and the silica particles in this example in accordance with the above methods. The measurement results are shown in Table 1-1.

Example 1-13

The operation of Example 1 was repeated except that 20 g of ammonium carbamate (2.6 mass % based on inorganic oxide particles contained in the dispersion) was used in place of the dry ice. Various measurements were made on the dispersion and the silica particles in this example in accordance with the above methods. The measurement results are shown in Table 1-1.

Example 1-14

The operation of Example 1 was repeated except that the drying temperature was set to 150° C. When the nitrogen content was measured, it was 0.01%.

Various measurements were made on the dispersion and the silica particles in this example in accordance with the above methods. The measurement results are shown in Table 1-1.

Example 1-15

The operation of Example 2 was repeated except that the drying temperature was set to 150° C. When the nitrogen content was measured, it was 0.01%.

Various measurements were made on the dispersion and the silica particles in this example in accordance with the above methods. The measurement results are shown in Table 1-1.

Comparative Example 1-1

When filtration was carried out without adding dry ice and without carrying out the subsequent stirring operation in Example 1-1, the dispersion passed through a filter paper and silica could not be collected. Therefore, after the obtained dispersion was concentrated under reduced pressure to remove the organic solvent to a certain extent, the dispersion was vacuum dried at 100° C. for 16 hours and then calcined at 900° C. in air for 10 hours to obtain silica particles.

Various measurements were made on the dispersion and the silica particles in this example in accordance with the above methods. The measurement results are shown in Table 1-1.

Reference Example 1-1

A dispersion of silica particles was obtained by mixing 10 g of the dried and calcined silica particles obtained in the above Example 1-1 with 90 g of pure water and stirring the mixture for 1 hour. When this dispersion was filtered under reduced pressure by using a quantitative filter paper (hold particle diameter of 7 μm), the dispersion passed through a filter paper and silica particles could not be collected.

Then, after the above dispersion was vacuum dried at room temperature and the dispersion medium was distilled off to a certain extent, the dispersion was vacuum dried at 100° C. for 16 hours and then calcined at 900° C. in air for 10 hours to obtain silica particles. Various measurements were made on the silica particles in accordance with the above methods. The measurement results are shown in Table 1-1.

Reference Example 1-2

A dispersion of silica particles was obtained by mixing 10 g of the dried and calcined silica particles obtained in the above Example 1-1 with 90 g of a 5 mass % aqueous solution of ammonium carbonate and stirring the mixture for 1 hour. When this dispersion was filtered under reduced pressure by using a quantitative filter paper (hold particle diameter of 7 µm), a silica cake was collected. At this point, the filtrate was transparent.

The above silica cake was vacuum dried at 100° C. for 16 hours and then calcined at 900° C. in air for 10 hours to collect 10 g of silica particles.

It is understood from the results shown in Table 1-1 below that the inorganic oxide particles obtained by the production method of the present invention have extremely low crush strength and the formation of a firm agglomerate requiring a disintegration treatment is prevented in the step of concentrating a dispersion of the inorganic oxide particles and the drying step after concentration.

Production of Surface Treated Inorganic Oxide Particles

Example 1-16

400 g of silica particles which had been dried at 100° C. for 6 hours and obtained in the same manner as in the above Example 1-1 was placed into the vessel of a 20-L mixer and heated at 250° C. at the same time as the substitution of the inside of the vessel by nitrogen. After the circulation of nitrogen was continued at a rate of 10 L/min for 15 minutes, the vessel was sealed up, and steam was introduced at an inside partial pressure of the vessel of 60 kPa. 120 g of hexamethyldisilazane (30 parts by mass based on 100 parts by mass of the silica particles) was sprayed upon the silica particles from a one-fluid nozzle while the content of the vessel was stirred, and agitation was continued for 60 minutes to carryout a surface treatment. After the vessel of the mixer was opened to substitute the atmosphere by a nitrogen gas, the surface treated silica particles were taken out.

The hydrophobicity and crush strength values of the silica particles before and after the surface treatment in this example were evaluated by the above methods. The evaluation results are shown in Table 1-2.

TABLE 1-1

| | Dispersion | Concentrate Concentration | After drying | | After calcination | | | Content of metal | | |
|---|---|---|---|---|---|---|---|---|---|---|
| | Median diameter | of inorganic oxide | Median diameter | Variation coefficient | Median diameter | Variation coefficient | Crush strength | element (ppm) | | |
| | (µm) | (mass %) | (µm) | (%) | (µm) | (%) | (N) | Na | Al | Fe |
| Ex. 1-1 | 0.090 | 57 | 0.088 | 20 | 0.082 | 21 | 0.21 | 0.7 | 0.1 | 0.1 |
| Ex. 1-2 | 0.090 | 55 | 0.089 | 19 | 0.083 | 20 | 0.19 | 0.7 | 0.1 | 0.1 |
| Ex. 1-3 | 0.089 | 56 | 0.087 | 19 | 0.082 | 21 | 0.19 | 0.8 | 0.2 | 0.1 |
| Ex. 1-4 | 0.089 | 59 | 0.089 | 18 | 0.083 | 19 | 0.22 | 0.7 | 0.1 | 0.1 |
| Ex. 1-5 | 0.40 | 58 | 0.42 | 16 | 0.38 | 16 | 0.21 | 0.9 | 0.2 | 0.2 |
| Ex. 1-6 | 0.82 | 52 | 0.83 | 14 | 0.78 | 15 | 0.19 | 0.9 | 0.2 | 0.1 |
| Ex. 1-7 | 0.82 | 51 | 0.84 | 15 | 0.78 | 15 | 0.19 | 0.9 | 0.2 | 0.1 |
| Ex. 1-8 | 0.83 | 65 | 0.83 | 14 | 0.78 | 15 | 0.19 | 0.9 | 0.2 | 0.2 |
| Ex. 1-9 | 0.61 | 62 | 0.61 | 10 | 0.58 | 11 | 0.21 | 1.0 | 0.2 | 0.2 |
| Ex. 1-10 | 0.14 | 58 | 0.13 | 6 | 0.14 | 7 | 0.23 | 1.0 | 0.2 | 0.2 |
| Ex. 1-11 | 0.40 | 59 | 0.41 | 15 | 0.38 | 16 | 0.21 | 0.8 | 0.1 | 0.1 |
| Ex. 1-12 | 0.090 | 54 | 0.089 | 19 | 0.082 | 21 | 0.20 | 0.7 | 0.1 | 0.1 |
| Ex. 1-13 | 0.090 | 55 | 0.089 | 18 | 0.082 | 20 | 0.19 | 0.8 | 0.1 | 0.1 |
| Ex. 1-14 | 0.090 | 57 | 0.088 | 20 | 0.082 | 21 | 0.20 | 0.7 | 0.1 | 0.1 |
| Ex. 1-15 | 0.090 | 55 | 0.089 | 19 | 0.083 | 20 | 0.19 | 0.7 | 0.1 | 0.1 |
| C.Ex. 1-1 | 0.089 | — | 0.095 | 42 | 4.5 | 95 | 1.3 | 1.1 | 0.2 | 0.1 |
| R.Ex. 1-1 | 0.090 | — | 0.096 | 41 | 4.4 | 96 | 1.4 | 1.1 | 0.2 | 0.1 |

Ex.: Example
C.Ex.: Comparative Example
R.Ex.: Reference Example

Example 1-17

The operation of the above Example 1-16 was repeated except that 400 g of silica particles which had been dried at 100° C. for 6 hours and obtained in the same manner as in the above Example 1-11 was used. The evaluation results are shown in Table 1-2.

Example 1-18

140 g of silica particles which had been dried at 100° C. for 6 hours and obtained in the same manner as in the above Example 1-11 and 700 g of toluene were placed into a 1-L four-necked flask and stirred at room temperature. 1.68 g of amino modified oil (1.2 parts by mass based on 100 parts by mass of the silica particles) (X-22-161A of Shin-Etsu Chemical Co., Ltd.) was added into the flask and heated at 110° C. under reflux for 1 hour. Thereafter, the solvent was distilled off under reduced pressure to obtain surface treated silica particles.

The hydrophobicity and crush strength values of the silica particles before and after the surface treatment in this example were evaluated by the above methods. The evaluation results are shown in Table 1-2.

Example 1-19

140 g of silica particles which had been dried at 100° C. for 6 hours and obtained in the same manner as in the above Example 1-11 and 700 g of toluene were placed into a 1-L four-necked flask and stirred at room temperature. 3.76 g of decyltrimethoxysilane (2.7 parts by mass based on 100 parts by mass of the silica particles) was added into the flask and heated at 110° C. under reflux for 1 hour. Thereafter, the solvent was distilled off under reduced pressure to obtain surface treated silica particles.

The hydrophobicity and crush strength values of the silica particles before and after the surface treatment in this example were evaluated by the above methods. The evaluation results are shown in Table 1-2.

TABLE 1-2

| | Hydrophobicity (vol %) | | Crush strength (N) | |
|---|---|---|---|---|
| | Before surface treatment | After surface treatment | Before surface treatment | After surface treatment |
| Ex. 1-16 | 0 | 62 | 0.21 | 0.02 |
| Ex. 1-17 | 0 | 65 | 0.21 | 0.02 |
| Ex. 1-18 | 0 | 59 | 0.21 | 0.02 |
| Ex. 1-19 | 0 | 50 | 0.21 | 0.02 |

Production of Surface Treated Inorganic Oxide Particles

Example 2-1

150 g of 15 mass % ammonia water (1.2 mass % of ammonia based on the mass of a metal alkoxide which will be described hereinafter) as a basic catalyst and 1,040 g of methanol (27 mass % based on the mass of the obtained inorganic oxide particle dispersion) as an organic solvent were placed into a 10-L four-necked flask and stirred at 35° C.

1,940 g of tetramethoxysilane as a metal alkoxide and 700 g of 5 mass % ammonia water (1.8 mass % of ammonia based on the mass of the metal alkoxide, a total of 3.0 mass % including ammonia contained in the ammonia water placed previously) as a basic catalyst were each independently added directly into the obtained liquid a little at a time. The addition speed was controlled to ensure that the addition ended in 5 hours. The mass of the inorganic oxide particle dispersion obtained by the above recipe was 3,830 g, and the concentration of silica in the dispersion was 20 mass % (766 g of silica).

10 minutes after the start of addition, the reaction liquid was clouded, thereby confirming the proceeding of the reaction.

After the end of addition, ageing was carried out for 0.5 hour and then 230 g of hexamethyldisilazane (30 mass % based on silica contained in the dispersion) as a surface treating agent was added. After addition, stirring was carried out at 35° C. for 1 hour to make a surface treatment on the inorganic oxide particle dispersion.

1,530 g of a 10 mass % ammonium hydrogen carbonate aqueous solution (153 g of ammonium hydrogen carbonate, 20 mass % based on silica contained in the dispersion) was added to the obtained dispersion containing the surface treated inorganic oxide particles. After the addition of the ammonium hydrogen carbonate aqueous solution, stirring was continued for another 2 hours.

The obtained dispersion after the addition of the ammonium hydrogen carbonate aqueous solution was filtered under reduced pressure to collect a cake. At this point, a filtration leak was not confirmed.

The cake collected by the above filtration was dried under reduced pressure at 100° C. for 24 hours to obtain 790 g of surface treated silica particles.

Various measurements were made on the dispersion and the silica particles in this example in accordance with the above methods. The measurement results are shown in Table 2-1.

Example 2-2

The operation of Example 2-1 was repeated except that the stirring time after the addition of a 10 mass % ammonium hydrocarbon carbonate aqueous solution was changed to 24 hours. The measurement results are shown in Table 2-1.

Example 2-3

The operation of Example 2-1 was repeated except that the stirring temperature after the addition of hexamethyldisilazane was changed to 60° C. The measurement results are shown in Table 2-1.

Example 2-4

The operation of Example 2-1 was repeated except that drying was carried out at 25° C. under atmospheric pressure for 24 hours and then at 25° C. under reduced pressure for 24 hours after filtration. The measurement results are shown in Table 2-1.

Example 2-5

The operation of Example 2-1 was repeated except that 780 g of methanol and 260 g of isopropyl alcohol were used as organic solvents. The measurement results are shown in Table 2-1.

Example 2-6

210 g of 25 mass % ammonia water (3.1 mass % of ammonia based on the mass of a metal alkoxide) as a basic catalyst and 310 g of methanol and 710 g of isopropyl alcohol (26.8 mass % based on the mass of the obtained inorganic oxide particle dispersion) as organic solvents were placed into a 5-L four-necked flask and stirred at 40° C. 26 g of tetraethoxysilane as a metal alkoxide was added dropwise to the obtained liquid. 10 minutes after addition, the reaction liquid was clouded, thereby confirming the proceeding of the reaction.

A solution consisting of 1,650 g of tetramethoxysilane as a metal alkoxide and 170 g of methanol (4.5 mass % based on the mass of the inorganic oxide particle dispersion, a total of 31 mass % of the alcohols) as an organic solvent and 730 g of 25% ammonia water (10.9 mass % of ammonia based on the mass of the metal alkoxide, a total of 14 mass % including ammonia contained in the ammonia water placed previously) as a basic catalyst were each independently added directly into the obtained dispersion a little at a time. The addition speed was controlled to ensure that addition ended in 2 hours.

The mass of the inorganic oxide particle dispersion obtained by the above recipe was 3,806 g, and the concentration of silica contained in the dispersion was 20 mass % (753 g of silica).

After the end of addition, ageing was carried out for 0.5 hour and then 226 g of hexamethyldisilazane (30 mass % based on silica contained in the dispersion) as a surface treating agent was added. After addition, stirring was carried out at 35° C. for 1 hour to make a surface treatment on the inorganic oxide particle dispersion.

1,510 g of a 10 mass % aqueous solution of ammonium hydrogen carbonate (151 g of ammonium hydrogen carbonate, 20 mass % based on silica contained in the dispersion) was added to the obtained dispersion containing the surface treated inorganic oxide particles. After the addition of the ammonium hydrogen carbonate aqueous solution, stirring was continued for another 2 hours.

The above dispersion after the addition of the ammonium hydrogen carbonate aqueous solution was filtered under reduced pressure to collect a cake. At this point, a filtration leak was not confirmed.

The cake collected by the above filtration was dried under reduced pressure at 100° C. for 24 hours to obtain 776 g of surface treated silica particles.

Various measurements were made on the dispersion and the silica particles in this example in accordance with the above methods. The measurement results are shown in Table 2-1.

Example 2-7

The operation of Example 2-1 was repeated except that 77.6 g of dimethyl silicone oil (10 mass % based on silica contained in the dispersion) was added in place of hexamethyldisilazane. The measurement results are shown in Table 2-1.

Example 2-8

The operation of Example 2-1 was repeated except that the step of adding 114.9 g of decyltrimethoxysilane (15 mass % based on silica contained in the dispersion) as a surface treating agent and ageing for 1 hour were added before the addition of hexamethyldisilazane. The measurement results are shown in Table 2-1.

Example 2-9

The operation of Example 2-6 was repeated except that centrifugal filtration at a revolution of 1,000 rpm was carried out by using a filter cloth (draft quantity of 1.2 cc/(cm2·sec)) in place of filtration under reduced pressure. The measurement results are shown in Table 2-1.

Example 2-10

The operation of Example 2-1 was repeated except that the amount of the ammonium hydrogen carbonate aqueous solution was changed to 1,149 g (114.9 g of ammonium hydrogen carbonate, 15 mass % based on silica contained in the dispersion). The measurement results are shown in Table 2-1.

Example 2-11

The operation of Example 2-1 was repeated except that 153 g of ammonium hydrogen carbonate (20 mass % based on silica contained in the dispersion) was added as a solid and not as an aqueous solution and the stirring time after the addition of ammonium hydrogen carbonate was changed to 72 hours. The measurement results are shown in Table 2-1.

Example 2-12

The operation of Example 2-1 was repeated except that 383 g of dry ice (50 mass % of $CO_2$ based on silica contained in the dispersion) was added in place of the ammonium carbonate aqueous solution.

The filtration operation could be carried out without a problem except that there was a slight filtration leak in the initial stage of the filtering step of this example.

The measurement results are shown in Table 2-1.

Example 2-13

The operation of Example 2-2 was repeated except that the amount of the ammonium carbonate aqueous solution was changed to 1,530 g (153 g of ammonium hydrogen carbonate, 20 mass % based on silica contained in the dispersion). The measurement results are shown in Table 2-1.

Example 2-14

The operation of Example 2-1 was repeated except that the amount of the ammonium hydrogen carbonate aqueous solution was changed to 383 g (38.3 g of ammonium hydrogen carbonate, 5 mass % based on silica contained in the dispersion).

Although the silica particle contained in the dispersion passed through a filter paper in the initial stage of the filtering step and filtration took long, a cake was collected. The collected cake was dried at 100° C. under reduced pressure for 24 hours to obtain 75 g of surface treated silica particles.

Various measurements were made on the dispersion and the silica particles in this example in accordance with the above methods. The measurement results are shown in Table 2-1.

Example 2-15

The operation of Example 2-1 was repeated except that the amount of the ammonium hydrogen carbonate aqueous solution was changed to 766 g (76.6 g of ammonium hydrogen carbonate, 10 mass % based on silica contained in the dispersion).

Although the silica particle contained in the dispersion passed through a filter paper in the initial stage of the filtering step and filtration took long, a cake was collected. The collected cake was dried at 100° C. under reduced pressure for 24 hours to obtain 265 g of surface treated silica particles.

Various measurements were made on the dispersion and the silica particles in this example in accordance with the above methods. The measurement results are shown in Table 2-1.

Example 2-16

The operation of Example 2-1 was repeated except that 153 g of ammonium hydrogen carbonate (20 mass % based on silica contained in the dispersion) was added as a solid and not as an aqueous solution.

Although most of the silica particles contained in the dispersion passed through a filter paper in the filtering step of this example, a cake could be collected.

Various measurements were made on the dispersion and the silica particles in this example in accordance with the above methods. The measurement results are shown in Table 2-1.

Example 2-17

The operation of Example 2-1 was repeated except that 153 g of dry ice (20 mass % of $CO_2$ based on silica contained in the dispersion) was added in place of the ammonium hydrogen carbonate aqueous solution.

Although most of the silica particles contained in the dispersion passed through a filter paper in the filtering step of this example, a cake could be collected. The collected cake was dried at 100° C. under reduced pressure for 24 hours to obtain 68 g of surface treated silica particles.

Various measurements were made on the dispersion and the silica particles in this example in accordance with the above methods. The measurement results are shown in Table 2-1.

Example 2-18

The operation of Example 2-1 was repeated except that 1,530 g of 10 mass % ammonium carbamate (153 g of ammonium carbamate, 20 mass % based on silica contained in the dispersion) was added in place of the ammonium hydrogen carbonate aqueous solution.

In the filtering step of this example, a filtration leak was not seen.

Various measurements were made on the dispersion and the silica particles in this example in accordance with the above methods. The measurement results are shown in Table 2-1.

Example 2-19

The operation of Example 2-1 was repeated except that the drying temperature was changed to 150° C. When the nitrogen content of the obtained silica particles, it was 0.01 mass %.

Various measurements were made on the dispersion and the silica particles in this example in accordance with the above methods. The measurement results are shown in Table 2-1.

Comparative Example 2-1

When filtration was carried out without adding an ammonium hydrogen carbonate aqueous solution and without carrying out the subsequent stirring operation in the above Example 2-1, the dispersion passed through a filter paper and silica could not be collected. Therefore, the obtained dispersion was concentrated under reduced pressure to obtain silica.

Various measurements were made on the dispersion and the silica particles in this example in accordance with the above methods. The measurement results are shown in Table 2-1.

Reference Example 2-1

The operation of Example 2-1 was repeated except that hexamethyldisilazane was not added and the subsequent stirring operation was not carried out.

The measurement results are shown in Table 2-1.

As obvious from Table 2-1, it is understood that surface treated inorganic oxide particles having low crush strength and excellent disintegration properties are obtained by the method in the above Examples 2-1 to 2-19. In the method of the present invention, particularly in Examples 2-1 to 2-10, particles can be easily collected from a dispersion of surface treated inorganic oxide particles by simple filtration at a high efficiency.

TABLE 2-1

| | Before surface treatment | Surface treatment, after drying | | | | | | | Yield of surface treated inorganic |
|---|---|---|---|---|---|---|---|---|---|
| | Median diameter | Median diameter | Variation coefficient | Hydrophobicity | Crush strength | Content of metal element (ppm) | | | oxide particles |
| | ($\mu$m) | ($\mu$m) | (%) | (vol %) | (N) | Na | Al | Fe | (g) |
| Ex. 2-1 | 0.090 | 0.090 | 20 | 51 | 0.02 | 0.9 | 0.2 | 0.1 | 790 |
| Ex. 2-2 | 0.090 | 0.090 | 20 | 61 | 0.01 | 0.9 | 0.2 | 0.1 | 775 |
| Ex. 2-3 | 0.090 | 0.090 | 20 | 55 | 0.02 | 1.0 | 0.1 | 0.1 | 771 |
| Ex. 2-4 | 0.090 | 0.090 | 20 | 50 | 0.04 | 1.0 | 0.2 | 0.1 | 766 |
| Ex. 2-5 | 0.40 | 0.40 | 15 | 50 | 0.02 | 1.0 | 0.2 | 0.1 | 765 |
| Ex. 2-6 | 0.82 | 0.82 | 14 | 50 | 0.03 | 0.9 | 0.2 | 0.1 | 691 |
| Ex. 2-7 | 0.090 | 0.090 | 20 | 27 | 0.04 | 1.1 | 0.2 | 0.2 | 780 |
| Ex. 2-8 | 0.090 | 0.090 | 20 | 64 | 0.01 | 1.0 | 0.2 | 0.2 | 775 |
| Ex. 2-9 | 0.090 | 0.090 | 20 | 50 | 0.02 | 0.9 | 0.2 | 0.1 | 755 |
| Ex. 2-10 | 0.090 | 0.090 | 20 | 51 | 0.02 | 1.0 | 0.2 | 0.1 | 758 |
| Ex. 2-11 | 0.090 | 0.090 | 20 | 59 | 0.02 | 0.9 | 0.2 | 0.2 | 778 |
| Ex. 2-12 | 0.090 | 0.090 | 20 | 58 | 0.02 | 0.8 | 0.2 | 0.2 | 740 |

TABLE 2-1-continued

|  | Before surface treatment | Surface treatment, after drying | | | | | | | Yield of surface treated inorganic |
|---|---|---|---|---|---|---|---|---|---|
|  | Median diameter | Median diameter | Variation coefficient | Hydrophobicity | Crush strength | Content of metal element (ppm) | | | oxide particles |
|  | (μm) | (μm) | (%) | (vol %) | (N) | Na | Al | Fe | (g) |
| Ex. 2-13 | 0.090 | 0.091 | 20 | 60 | 0.02 | 0.9 | 0.2 | 0.2 | 791 |
| Ex. 2-14 | 0.090 | 0.092 | 23 | 49 | 0.06 | 0.8 | 0.2 | 0.1 | 75 |
| Ex. 2-15 | 0.090 | 0.091 | 21 | 49 | 0.05 | 0.9 | 0.2 | 0.1 | 265 |
| Ex. 2-16 | 0.090 | 0.091 | 21 | 50 | 0.05 | 0.9 | 0.2 | 0.1 | 125 |
| Ex. 2-17 | 0.090 | 0.091 | 21 | 50 | 0.05 | 0.8 | 0.2 | 0.1 | 68 |
| Ex. 2-18 | 0.090 | 0.090 | 20 | 52 | 0.02 | 0.9 | 0.2 | 0.1 | 756 |
| Ex. 2-19 | 0.090 | 0.090 | 20 | 52 | 0.02 | 0.9 | 0.2 | 0.1 | 788 |
| C.Ex. 2-1 | 0.090 | 0.095 | 35 | 48 | 0.18 | 1.1 | 0.2 | 0.1 | 770*) |
| R.Ex. 2-1 | 0.090 | 0.089 | 20 | 0 | 0.21 | 1.0 | 0.2 | 0.1 | 760 |

Ex.: Example
C.Ex.: Comparative Example
R.Ex.: Reference Example
*)The method of collecting silica in Comparative Example 2-1 differs from the method in other examples.

Example 2-20

The agglomeration degree of the surface treated silica particles obtained in the above Example 2-2 without a pretreatment (disintegration) and after the pretreatment was made under the following conditions was measured in accordance with the above method. The results are shown in Table 2-2.
(Pretreating Method)
15 g of silica and 15 g of glass beads having a diameter of 5 mm (BZ-5 glass bead of As One Corporation) were put into the I-Boy wide-mouth bottle having a capacity of 100 mL (trade name, manufactured by As One Corporation), and the bottle was set in a vertical shaking apparatus (SA-31 of Yamato Scientific Co., Ltd.) to shake it at an amplitude of 5 cm and a rate of 270 times/min for 30 minutes.
The disintegration conditions were very mild.

Comparative Example 2-2

Surface treated silica particles were prepared in accordance with Example 1 of JP-A 2000-44226.
2,297 g of a silica dispersion before a surface treatment obtained in the same manner as in Example 2-1 was placed into a 5-L four-necked flask, 1,600 g of water was added when 678 g of methanol was distilled off by heating at 60 to 70° C., and then 195 g of methanol was distilled off by heating at 70 to 90° C. to obtain an aqueous dispersion of silica fine particles.
115.8 g of methyl trimethoxysilane and 46.6 g of 5.4 mass % ammonia water were added dropwise to this aqueous dispersion at room temperature over 0.5 hour and stirring was continued for 15 hours after addition to carry out the surface treatment of the silica fine particles.
After 1,000 g of methyl isobutyl ketone was added to the dispersion containing surface treated silica obtained as described above, the resulting mixture was heated at 80 to 110° C. to distill off 1,338 g of both methanol and water over 7 hours.
357.6 g of hexamethyldisilazane was added to the obtained dispersion at room temperature and heated at 120° C. to carry out a reaction for 3 hours so as to trimethylsilylate the surfaces of silica particles. Thereafter, the solvent was distilled off under reduced pressure to obtain 520 g of surface treated silica.

The agglomeration degree without a pretreatment and after the pretreatment was measured in the same manner as in the above Example 2-20 except that the surface treated silica particles obtained above were used. The results are shown in Table 2-2.

Comparative Example 2-3

Surface treated silica particles were prepared in accordance with Synthesis Example 1 of JP-A 2002-108001.
600 g of a silica dispersion (120 g of silica) before a surface treatment obtained in the same manner as in the above Example 2-1 was heated to remove methanol, and toluene was added and heated to remove water. 48 g of hexamethyldisilazane (40 mass % based on silica contained in silica slurry) was added to the resulting mixture, heated at 120° C. for 2 hours under agitation and further heated to remove toluene. The resulting mixture was dried at 100° C. under reduced pressure for 24 hours to obtain 107 g of surface treated silica.
The agglomeration degree without a pretreatment and after the pretreatment was measured in the same manner as in the above Example 2-20 except that the surface treated silica particles obtained above were used. The results are shown in Table 2-2.

TABLE 2-2

|  | Agglomeration degree (%) | |
|---|---|---|
|  | Without pretreatment | After pretreatment |
| Example 2-20 | 44 | 27 |
| Comparative Example 2-2 | 63 | 66 |
| Comparative Example 2-3 | 69 | 78 |

Production of Surface Treated Inorganic Oxide Particles

Example 3-1

(1) Reaction Step 150 g of 15 mass % ammonia water (1.2 mass % based on the mass of a metal alkoxide which will be described hereinafter) as a basic catalyst and 1,040 g of methanol (27 mass % based on the mass of an inorganic oxide particle dispersion produced by a reaction) as an organic solvent were placed into a 10-L four-necked flask and stirred at 35° C. 1,940 g of tetramethoxysilane as a metal alkoxide and 700 g of 5 mass % ammonia water (1.8 mass % of ammonia based on the mass of the metal alkoxide, a total of 3.0 mass % including the ammonia water placed previously) as a basic catalyst were each independently added directly into the resulting liquid a little at a time. The addition speed was controlled to ensure that the addition ended in 5 hours. 10 minutes after the start of addition, the reaction liquid was clouded, thereby confirming the proceeding of a reaction. After the end of addition, ageing was carried out at 35° C. for 0.5 hour to obtain a dispersion of inorganic oxide particles.

The mass of the dispersion of inorganic oxide particles was 3,830 g, and the concentration of silica in the dispersion was 20 mass % (766 g of silica).

(2) First Surface Treating Step 230 g of hexamethyldisilazane (30 mass % based on silica contained in the dispersion) as a surface treating agent was added to the dispersion obtained in the above step (1) and stirred at 35° C. for 1 hour.

(3) Coagulant Adding Step 1,530 g of a 10 mass % ammonium hydrogen carbonate aqueous solution (153 g of ammonium hydrogen carbonate, 20 mass % based on silica contained in the dispersion) as a coagulant was added to the surface treated silica dispersion obtained in the above step (2) and then stirred at 35° C. for 2 hours.

(4) Particle Collection Step

The dispersion after the addition of the coagulant obtained in the above step (3) was filtered under reduced pressure to obtain a cake. At this point, a filtration leak was not confirmed.

(5) Particle Drying Step

The cake collected in the above step (4) was dried under reduced pressure at 150° C. for 24 hours to obtain 790 g of silica particles after the first surface treatment.

The steps (1) to (5) are the same as in the above Example 2-1.

(6) Second Surface Treating Step

The silica particles after the first surface treatment obtained in the above step (5) were placed into a 20-L pressure vessel and heated up to 230° C. After the inside of the vessel was substituted by a nitrogen atmosphere, it was sealed up under atmospheric pressure, and 16 g of water was sprayed upon the particles under agitation. Thereafter, stirring was continued for 15 minutes, depressurization was carried out, and 95 g of hexamethyldisilazane was sprayed upon the particles. After stirring was further continued for another 1 hour, 400 g of silica particles after a second surface treatment were obtained by depressurization.

Various measurements were made on the obtained silica particles in accordance with the above methods. The measurement results are shown in Table 3-1.

Example 3-2

Silica particles after the second surface treatment were obtained in the same manner as in Example 3-1 except that the second surface treating step (6) was changed to the following step (6') in the above Example 3-1. Various measurements were made on the obtained silica particles in accordance with the above methods. The measurement results are shown in Table 3-1.

(6') Second Surface Treating Step

Alternative Method 1

The silica particles after the first surface treatment obtained in the step (5) were placed into a 20-L pressure vessel and heated up to 230° C. After the inside of the vessel was substituted by a nitrogen atmosphere, it was sealed up under atmospheric pressure, and 50 g of methyltrimethoxysilane was sprayed upon the particles under agitation. After stirring was continued for 1 hour, depressurization was carried out, 16 g of water was sprayed upon the particles, and stirring was continued for 15 minutes. After depressurization, 95 g of hexamethyldisilazane was sprayed upon the particles, and stirring was further continued for another 1 hour. Then, 240 g of silica particles after the second surface treatment were obtained by depressurization.

Example 3-3

Silica particles after the second surface treatment were obtained in the same manner as in Example 3-1 except that the second surface treating step (6) was changed to the following step (6") in the above Example 3-1. Various measurements were made on the obtained silica particles in accordance with the above methods. The measurement results are shown in Table 3-1.

(6") Second Surface Treating Step

Alternative Method 2

The silica particle after the first surface treatment obtained in the above step (5) were placed into a 20-L pressure vessel and heated up to 230° C. After the inside of the vessel was substituted by a nitrogen atmosphere, it was sealed up under atmospheric pressure, and 16 g of water was sprayed upon the particles under agitation. Thereafter, stirring was continued for 15 minutes, depressurization was carried out, and 95 g of hexamethyldisilazane was sprayed upon the particles. After stirring was continued for 1 hour, depressurization was carried out, 3 g of silicone oil having a viscosity of 50 cps was further sprayed upon the particles, and stirring was further continued for another 1 hour. Then, 300 g of silica particles after the second surface treatment was obtained by depressurization.

Comparative Example 3-1

Attempts were made to carry out the particle collection step (4) without carrying out the coagulant addition step (3) in the above Example 3-1 but the particles passed through the a filter paper and could not be collected. Then, the solvent contained in the dispersion was removed under reduced pressure to collect silica. Thereafter, the operation of the second surface treating step (6) in Example 3-1 was repeated to obtain 600 g of surface treated silica particles. Various measurements were made on the obtained silica particles in accordance with the above methods. The measurement results are shown in Table 3-1.

Table 3-1 below shows the evaluation results of the particles obtained in the above Examples 3-1 to 3-3 and Comparative Example 3-1 as well as the evaluation results of the particles obtained in the above Comparative Examples 2-2 and 2-3 and the evaluation results of the particles obtained in the above Example 2-1 as Reference Example 3-1.

The coverages of the resin surface of the particles obtained in Comparative Examples 3-1, 2-2 and 2-3 were less than 5% which means that the particles rarely adhered to the surface of the resin. Therefore, as it was judged that the particles did not reach a practical level, the triboelectric charge quantity was not measured.

TABLE 3-1

| | Hydro-phobicity | Agglomeration | Amount of N | Content of metal element (ppm) | | | Surface coverage | Triboelectric charge quantity | | |
| --- | --- | --- | --- | --- | --- | --- | --- | --- | --- | --- |
| | | | | | | | | Rate of charge rise | Saturation triboelectric charge quantity | Charge stability |
| | (vol %) | degree (%) | (mass %) | Na | Al | Fe | (%) | (μc/g) | (μc/g) | (%) |
| Ex. 3-1 | 70 | 42 | 0.01 | 0.9 | 0.2 | 0.1 | 17 | 28 | 43 | 63 |
| Ex. 3-2 | 68 | 41 | 0.01 | 0.9 | 0.2 | 0.1 | 12 | 32 | 37 | 70 |
| Ex. 3-3 | 67 | 48 | 0.01 | 1.0 | 0.1 | 0.1 | 11 | 26 | 48 | 81 |
| Ex. 3-1 | 63 | 66 | 0.09 | 0.9 | 0.2 | 0.1 | Less than 5 | — | — | — |
| C. Ex. 2-2 | 64 | 66 | 0.09 | 1.1 | 0.2 | 0.2 | Less than 5 | — | — | — |
| C. Ex. 2-3 | 53 | 78 | 0.12 | 1.0 | 0.2 | 0.1 | Less than 5 | — | — | — |
| R. Ex. 3-1 (Ex. 2-1) | 61 | 46 | 0.01 | 0.9 | 0.2 | 0.1 | 9 | 17 | 26 | 34 |

Ex.: Example
C.Ex.: Comparative Example
R.Ex.: Reference Example

EFFECT OF THE INVENTION

According to the present invention, there is provided a method for easily producing inorganic oxide particles which do not agglomerate firmly and are excellent in flowability.

The inorganic oxide particles produced by the method of the present invention have weak agglomeration force and excellent disintegration properties. Further, although the coagulant used in the method of the present invention can be existent stably in a synthetic solution as it is or in the state of a derivative thereof, it is decomposed into carbon dioxide, ammonia and water by heating at about 35 to 60° C. Therefore, it can be easily decomposed and removed by heating at the time of drying. Consequently, according to the method of the present invention, there is no possibility that impurities derived from the coagulant remain in the product, thereby making it possible to obtain inorganic oxide particles having high purity. This is a great advantage as compared with a conventional method using a metal salt which readily remains in particles.

The inorganic oxide particles produced by the method of the present invention can be advantageously used as a filler for resins and rubbers or an abrasive.

When the inorganic oxide particles produced by the method of the present invention are surface treated inorganic oxide particles whose surfaces have been hydrophobized, the particles are hydrophobic as well as having excellent disintegration properties and a narrow particle size distribution. Therefore, they are useful as an external additive for electrophotographic toners.

The invention claimed is:

1. Surface treated inorganic oxide particles having a crush strength of 0.01 to 0.06N, said surface treated inorganic oxide particles being produced by a method comprising:
   coagulating a dispersion obtained by carrying out the hydrolysis reaction and the polycondensation reaction of a metal alkoxide in the presence of a basic catalyst by using of a mixture of water and an alcohol as a solvent;
   filtering the dispersion to obtain particles; and
   drying the particles, wherein
   the step of coagulating the dispersion is carried out by adding a coagulant comprising at least one compound selected from the group consisting of carbon dioxide, ammonium carbonate, ammonium hydrogen carbonate and ammonium carbamate to the dispersion,
   the step of coagulating the dispersion is carried out after the step of adding at least one surface treating agent selected from the group consisting of a silicone oil, a silane coupling agent and a silazane to the dispersion; and
   the inorganic oxide particles to be produced are surface treated inorganic oxide particles having a crush strength of 0.01 to 0.06N.

2. The surface treated inorganic oxide particles according to claim 1, wherein, after a sieve having an opening of 355 μm, a sieve having an opening of 250 μm and a sieve having an opening of 150 μm (all the sieves have a diameter of 75 mm based on JIS Z8801) are placed one upon another at intervals of 2 cm in this order from the top, 5 g of the particles is put on the top sieve and vibrated vertically at an amplitude of 1 mm and a frequency of 60 Hz for 15 seconds, the agglomeration degree calculated from the amounts of particles remaining on these sieves based on the following equation is 60% or less; and > wherein agglomeration degree(%)={(amount of remaining particles on top sieve+amount of remaining particles on middle sieve×0.6+amount of remaining particles on bottom sieve×0.2)}÷initial mass of surface treated inorganic oxide particles×100.

3. The surface treated inorganic oxide particles having a crush strength of 0.01 to 0.06N according to claim 1, wherein the surface treatment of the inorganic oxide particles is carried out by further adding at least one surface treating agent selected from the group consisting of a silicone oil, a silane coupling agent and a silazane to the dried inorganic oxide particles after the drying step.

4. Surface treated inorganic oxide particles having a crush strength of 0.01 to 0.06N, said surface treated inorganic oxide particles being produced by a method comprising:

coagulating a dispersion obtained by carrying out the hydrolysis reaction and the polycondensation reaction of a metal alkoxide in the presence of a basic catalyst by using of a mixture of water and an alcohol as a solvent;

filtering the dispersion to obtain particles; and drying the particles, wherein the step of coagulating the dispersion is carried out by adding a coagulant comprising at least one compound selected from the group consisting of carbon dioxide, ammonium carbonate, ammonium hydrogen carbonate and ammonium carbamate to the dispersion, wherein surface treatment of the inorganic oxide particles is carried out by adding at least one surface treating agent selected from the group consisting of a silicone oil, a silane coupling agent and a silazane to the dried oxide particles after the drying step; and the inorganic oxide particles to be produced are surface treated inorganic oxide particles having a crush strength of 0.01 to 0.06N.

* * * * *